(12) United States Patent
Lubelski et al.

(10) Patent No.: US 11,021,762 B2
(45) Date of Patent: Jun. 1, 2021

(54) DNA IMPURITIES IN A COMPOSITION COMPRISING A PARVOVIRAL VIRION

(71) Applicant: uniQure IP B.V., Amsterdam (NL)

(72) Inventors: Jacek Lubelski, Amsterdam (NL); Wilhelmus Theodorus Johannes Maria Christiaan Hermens, Amsterdam (NL)

(73) Assignee: UNIQURE IP B.V., Amsterdam (NL)

( * ) Notice: Subject to any disclaimer, the term of this patent is extended or adjusted under 35 U.S.C. 154(b) by 0 days.

(21) Appl. No.: 15/531,095

(22) PCT Filed: Nov. 27, 2015

(86) PCT No.: PCT/EP2015/077882
§ 371 (c)(1),
(2) Date: May 26, 2017

(87) PCT Pub. No.: WO2016/083560
PCT Pub. Date: Jun. 2, 2016

(65) Prior Publication Data
US 2017/0321290 A1    Nov. 9, 2017

(30) Foreign Application Priority Data
Nov. 28, 2014   (EP) ..................................... 14195464

(51) Int. Cl.
*C12Q 1/6851*   (2018.01)
*C12Q 1/70*     (2006.01)
*C12Q 1/6869*   (2018.01)

(52) U.S. Cl.
CPC ........... *C12Q 1/701* (2013.01); *C12Q 1/6851* (2013.01); *C12Q 1/6869* (2013.01); *C12N 2710/14021* (2013.01); *C12N 2710/14111* (2013.01); *C12N 2750/14111* (2013.01); *C12N 2750/14121* (2013.01)

(58) Field of Classification Search
CPC ........ G16B 30/00–30/20; G16B 99/00; C12N 250/14111; C12N 2750/14132; C12N 2750/14143; C12N 2750/14111; C12N 2710/14111; C12N 2710/14021; C12N 2750/14121; C12Q 1/701; C12Q 1/6869; C12Q 2535/122; C12Q 1/6851
See application file for complete search history.

(56) References Cited

U.S. PATENT DOCUMENTS

| 6,451,536 B1 * | 9/2002 | Fodor | ................. | B01J 19/0046 |
| | | | | 435/288.3 |
| 2010/0112669 A1 * | 5/2010 | Liu | ........................ | C12N 7/00 |
| | | | | 435/239 |

FOREIGN PATENT DOCUMENTS

| WO | WO-2011/112089 A2 | 9/2011 |
| WO | WO-2013/011611 A1 | 1/2013 |
| WO | WO-2013/113852 A1 | 8/2013 |
| WO | WO-2014/018080 A1 | 1/2014 |
| WO | WO-2014/144486 A2 | 9/2014 |

OTHER PUBLICATIONS

Lecomte et al., Advanced Characterization of DNA Molecules in rAAV Vector Preparations by Single-stranded Virus Next-generation Sequencing; Molecular Therapy—Nucleic Acids, vol. 4, e260, pp. 1-11, 2015.*
Kapranov et al. Native molecular state of adeno-associated viral vectors revealed by single-molecule sequencing. Human Gene Therapy, vol. 23, pp. 46-55, Jan. 2012. (Year: 2012).*
European Medicines Agency Report for Glybera, Procedure No. EMEA/H/C/002145, Jul. 19 2012, pp. 1-147, especially p. 20. (Year: 2012).*
Cogné et al. Exhaustive characterization of DNA contaminants in rAAV productions by next generation sequencing. ESGCT and NVGCT Collaborative Congress: The Hague—Oct. 23 to 26 Abstracts, 2014, p. A54, Abstract OR087. (Year: 2014).*
Wright, J.F. Product-related impurities in clinical-grade recombinant AAV vectors: Characterization and risk assessment. Biomedicines, vol. 2, pp. 80-97, Mar. 3, 2014. (Year: 2014).*
Blouin et al., "Improving the rAAV production and purification: Towards the definition of a scaleable process", The Journal of Gene Medicine, Feb. 2004,vol. 6, pp. S223-S228.
Chadeuf et al., "Evidence for encapsidation of prokaryotic sequences during recombinant adeno-associated virus production and their in vivo persistence after vector delivery", Molecular Therapy, Oct. 2005, vol. 12, No. 4, pp. 744-753.
Halbert et al., "Capsid-expressing DNA in AAV vectors and its elimination by use of an oversize capsid gene for vector production", Gene Therapy, Apr. 2011, vol. 18, No. 4, pp. 411-417.
Hauck et al,. "Undetectable transcription of cap in a clinical AAV vector: implications for preformed capsid in immune responses", Molecular Therapy, Jan. 2009, vol. 17, No. 1, pp. 144-152.
J.E. Wright, "Manufacturing and characterizing AAV-based vectors for use in clinical studies", Gene Therapy, 2008, vol. 15, pp. 840-848.
Nony et al., "Evidence for packaging of rep-cap sequences into adeno-associated virus (AAV) type 2 capsids in the absence of inverted terminal repeats: a model for generation of rep-positive AAV particles", Journal of Virology, Jan. 2003, vol. 77, No. 1, pp. 776-781.
Nowrouzi et al., "Integration frequency and intermolecular recombination of rAAV vectors in non-human primate skeletal muscle and liver", Molecular Therapy, Jun. 2012, vol. 20, No. 6, pp. 1177-1186.

(Continued)

*Primary Examiner* — Jennifer Dunston
(74) *Attorney, Agent, or Firm* — Foley & Lardner LLP

(57) ABSTRACT

The current invention relates to nucleic acid impurities in a composition comprising a parvoviral vector. In particular, the current invention shows that DNA impurities are not randomly encapsulated within a parvoviral virion. The invention therefore relates to a method for identifying and quantifying a nucleic acid impurity in a composition comprising a parvoviral vector. Finally, the current invention relates to method of determining whether a composition comprising a parvoviral vector is regarded as clinically pure.

11 Claims, 10 Drawing Sheets
Specification includes a Sequence Listing.

(56) References Cited

OTHER PUBLICATIONS

Thorne et al., "Manufacturing recombinant adeno-associated viral vectors from producer cell clones", Human Gene Therapy, Jul. 2009, vol. 20, pp. 707-714.

Ye et al., "Clearance and characterization of residual HSV DNA in recombinant adeno-associated virus produced by an HSV complementation system", Gene Therapy, 2011, vol. 18, pp. 135-144.

International Search Report issued in International Patent Application No. PCT/EP2015/077882, dated Feb. 8, 2016.

Lin, Zhen et al.: "Detection of Murine Leukemia Virus in the Epstein-Barr Virus-Positive Human B-Cell Line JY, Using a Computational RNA-Seq-Based Exogenous Agent Detection Pipeline, PARSES," Journal of Virology, vol. 86, No. 6, Mar. 2012, p. 2970-2977.

Moraiti, Aikaterini et al.: European Medicines Agency Assessment Report for Glybera, Jul. 19, 2012, p. 1-147.

Nowrouzi, Ali et al.: Integration Frequency and intermolecular Recombination of rAAV Vectors in Non-human Primate Skeletal Muscle and Liver, Molecular Therapy, vol. 20, No. 6, Jun. 2012, 14 pages (p. 1177-1186, Supp. Figs. 1-4).

Penaud-Budloo, Magalie et al.:"Adeno-Associated Vims Vector Genomes Persist as Episomal Chromatin in Primate Muscle", Journal of Virology, vol. 82, No. 16, Aug. 2008, p. 7875-7885.

Wright, J.F. "AAV Empty Capsids: For Better or for Worse?" Molecular Therapy, vol. 22, No. 1, Jan. 2014, 2 pages.

\* cited by examiner

Fig. 4A

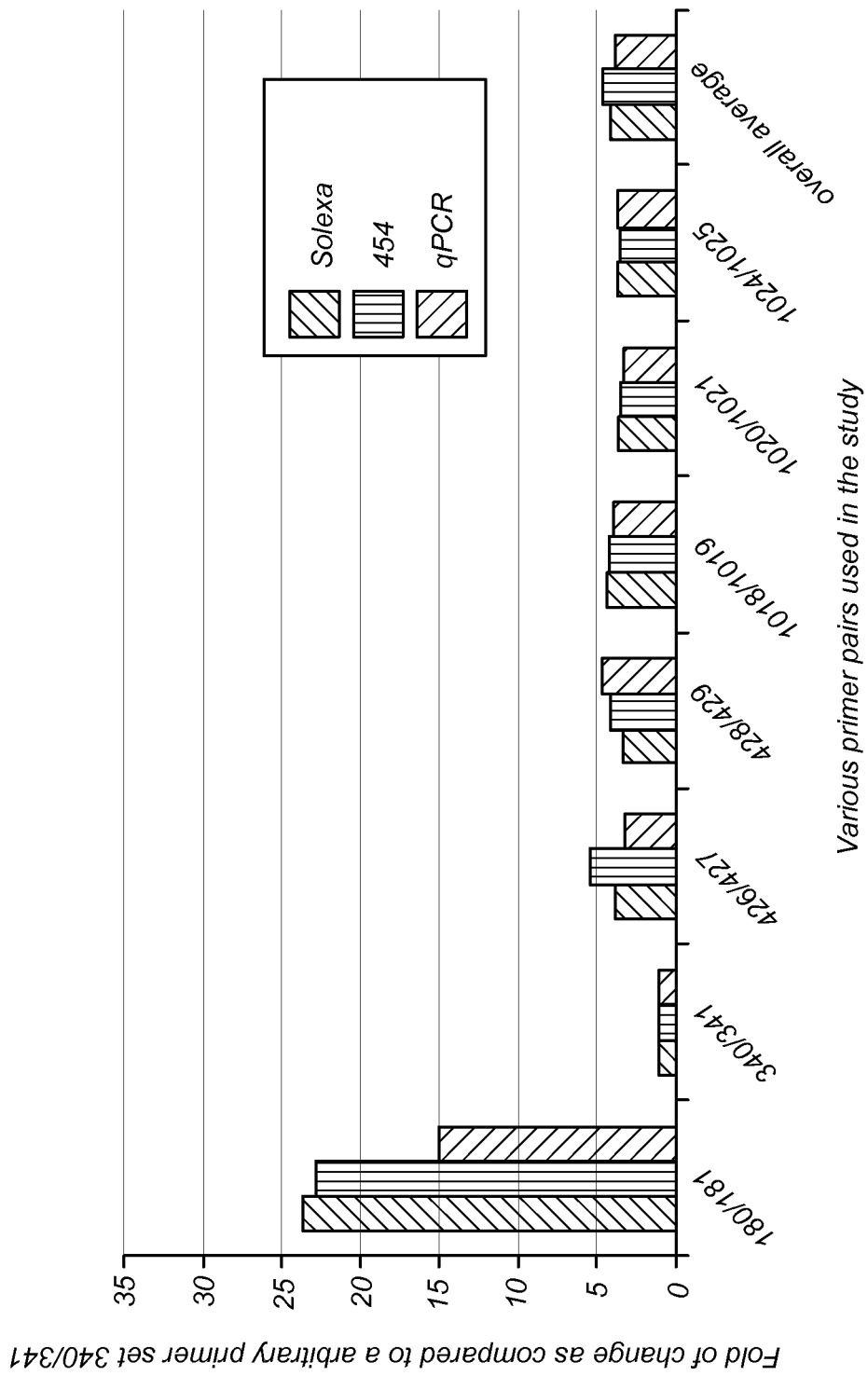

SEQUENCE LISTING

<160> NUMBER OF SEQ ID NOS: 34

<210> SEQ ID NO 1
<211> LENGTH: 145
<212> TYPE: DNA
<213> ORGANISM: adeno-associated virus 2
<220> FEATURE:
<221> NAME/KEY: misc_feature
<223> OTHER INFORMATION: upstream ITR

<400> SEQUENCE: 1
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcct                                          145

<210> SEQ ID NO 2
<211> LENGTH: 183
<212> TYPE: DNA
<213> ORGANISM: adeno-associated virus 2
<220> FEATURE:
<221> NAME/KEY: misc_feature
<223> OTHER INFORMATION: downstream ITR

<400> SEQUENCE: 2
gcgcggtacc ccatggagga acccctagtg atggagttgg ccactccctc tctgcgcgct      60
cgctcgctca ctgaggccgc ccgggcaaag cccgggcgtc gggcgacctt tggtcgcccg     120
gcctcagtga gcgagcgagc gcgcagagag ggagtggcca agatatccca tggggtaccg     180
cgc                                                                  183

<210> SEQ ID NO 3
<211> LENGTH: 2203
<212> TYPE: DNA
<213> ORGANISM: adeno-associated virus 5
<220> FEATURE:
<221> NAME/KEY: misc_feature
<223> OTHER INFORMATION: pDP5

<400> SEQUENCE: 3
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa ccctacctc aagtacaacc acgcggacgc cgagtttcag     300
gagaagctcg ccgacgacac atccttcggg ggaaacctcg gaaaggcagt ctttcaggcc     360
aagaaaaggg ttctcgaacc ttttggcctg gttgaagagg gtgctaagac ggccccctacc     420

-continued

```
ggaaagcgga tagacgacca ctttccaaaa agaaagaagg ctcggaccga agaggactcc      480
aagccttcca cctcgtcaga cgccgaagct ggacccagcg gatcccagca gctgcaaatc      540
ccagcccaac cagcctcaag tttgggagct gatacaatgt ctgcgggagg tggcggccca      600
ttgggcgaca ataaccaagg tgccgatgga gtgggcaatg cctcgggaga ttggcattgc      660
gattccacgt ggatggggga cagagtcgtc accaagtcca cccgaacctg ggtgctgccc      720
agctacaaca accaccagta ccgagagatc aaaagcggct ccgtcgacgg aagcaacgcc      780
aacgcctact ttggatacag cacccccctgg gggtactttg actttaaccg cttccacagc      840
cactggagcc cccgagactg gcaaagactc atcaacaact actggggctt cagaccccgg      900
tccctcagag tcaaaatctt caacattcaa gtcaaagagg tcacggtgca ggactccacc      960
accaccatcg ccaacaacct cacctccacc gtccaagtgt ttacggacga cgactaccag     1020
ctgccctacg tcgtcggcaa cgggaccgag ggatgcctgc cggccttccc tccgcaggtc     1080
tttacgctgc cgcagtacgg ttacgcgacg ctgaaccgcg acaacacaga aaatcccacc     1140
gagaggagca gcttcttctg cctagagtac tttcccagca agatgctgag aacgggcaac     1200
aactttgagt ttacctacaa cttgaggag gtgcccttcc actccagctt cgctcccagt     1260
cagaacctgt tcaagctggc caacccgctg gtggaccagt acttgtaccg cttcgtgagc     1320
acaaataaca ctggcggagt ccagttcaac aagaacctgg ccgggagata cgccaacacc     1380
tacaaaaact ggttcccggg gcccatgggc cgaacccagg gctggaacct gggctccggg     1440
gtcaaccgcg ccagtgtcag cgccttcgcc acgaccaata ggatggagct cgagggcgcg     1500
agttaccagg tgcccccgca gccgaacggc atgaccaaca cctccagggg cagcaacacc     1560
tatgccctgg agaacactat gatcttcaac agccagccgg cgaacccggg caccaccgcc     1620
acgtacctcg agggcaacat gctcatcacc agcgagagcg agacgcagcc ggtgaaccgc     1680
gtggcgtaca cgtcggcgg gcagatggcc accaacaacc agagctccac cactgccccc     1740
gcgaccggca cgtacaacct ccaggaaatc gtgcccggca gcgtgtggat ggagagggac     1800
gtgtacctcc aaggacccat ctgggccaag atcccagaga cggggggcgca ctttcacccc     1860
tctccggcca tgggcggatt cggactcaaa caccaccgc catgatgct catcaagaac     1920
acgcctgtgc ccggaaatat caccagcttc tcggacgtgc ccgtcagcag cttcatcacc     1980
cagtacagca ccgggcaggt caccgtggag atggagtggg agctcaagaa ggaaaactcc     2040
aagaggtgga acccagagat ccagtacaca aacaactaca acgaccccca gtttgtggac     2100
tttgcccccg acagcaccgg ggaatacaga accaccagac tatcggaaac ccgataccttt    2160
acccgacccc tttaacccat tcatgtcgca taccctcaat aaa                       2203
```

<210> SEQ ID NO 4
<211> LENGTH: 1876
<212> TYPE: DNA
<213> ORGANISM: adeno-associated virus 2
<220> FEATURE:
<221> NAME/KEY: CDS
<222> LOCATION: (11)..(1876)

<400> SEQUENCE: 4

```
cgcagccgcc atg ccg ggg ttt tac gag att gtg att aag gtc ccc agc       49
            Met Pro Gly Phe Tyr Glu Ile Val Ile Lys Val Pro Ser
              1               5                  10 gac ctt gac gag cat ctg ccc ggc att tct gac agc ttt gtg aac tgg       97
Asp Leu Asp Glu His Leu Pro Gly Ile Ser Asp Ser Phe Val Asn Trp
 15                  20                  25
```

```
gtg gcc gag aag gaa tgg gag ttg ccg cca gat tct gac atg gat ctg    145
Val Ala Glu Lys Glu Trp Glu Leu Pro Pro Asp Ser Asp Met Asp Leu
 30          35                  40                  45 aat ctg att gag cag gca ccc ctg acc gtg gcc gag aag ctg cag cgc    193
Asn Leu Ile Glu Gln Ala Pro Leu Thr Val Ala Glu Lys Leu Gln Arg
             50                  55                  60 gac ttt ctg acg gaa tgg cgc cgt gtg agt aag gcc ccg gag gcc ctt    241
Asp Phe Leu Thr Glu Trp Arg Arg Val Ser Lys Ala Pro Glu Ala Leu
                 65                  70                  75 ttc ttt gtg caa ttt gag aag gga gag agc tac ttc cac atg cac gtg    289
Phe Phe Val Gln Phe Glu Lys Gly Glu Ser Tyr Phe His Met His Val
             80                  85                  90 ctc gtg gaa acc acc ggg gtg aaa tcc atg gtt ttg gga cgt ttc ctg    337
Leu Val Glu Thr Thr Gly Val Lys Ser Met Val Leu Gly Arg Phe Leu
         95                 100                 105 agt cag att cgc gaa aaa ctg att cag aga att tac cgc ggg atc gag    385
Ser Gln Ile Arg Glu Lys Leu Ile Gln Arg Ile Tyr Arg Gly Ile Glu
110                 115                 120                 125 ccg act ttg cca aac tgg ttc gcg gtc aca aag acc aga aat ggc gcc    433
Pro Thr Leu Pro Asn Trp Phe Ala Val Thr Lys Thr Arg Asn Gly Ala
                130                 135                 140 gga ggc ggg aac aag gtg gtg gat gag tgc tac atc ccc aat tac ttg    481
Gly Gly Gly Asn Lys Val Val Asp Glu Cys Tyr Ile Pro Asn Tyr Leu
            145                 150                 155 ctc ccc aaa acc cag cct gag ctc cag tgg gcg tgg act aat atg gaa    529
Leu Pro Lys Thr Gln Pro Glu Leu Gln Trp Ala Trp Thr Asn Met Glu
        160                 165                 170 cag tat tta agc gcc tgt ttg aat ctc acg gag cgt aaa cgg ttg gtg    577
Gln Tyr Leu Ser Ala Cys Leu Asn Leu Thr Glu Arg Lys Arg Leu Val
175                 180                 185 gcg cag cat ctg acg cac gtg tcg cag acg cag gag cag aac aaa gag    625
Ala Gln His Leu Thr His Val Ser Gln Thr Gln Glu Gln Asn Lys Glu
190                 195                 200                 205 aat cag aat ccc aat tct gat gcg ccg gtg atc aga tca aaa act tca    673
Asn Gln Asn Pro Asn Ser Asp Ala Pro Val Ile Arg Ser Lys Thr Ser
                210                 215                 220 gcc agg tac atg gag ctg gtc ggg tgg ctc gtg gac aag ggg att acc    721
Ala Arg Tyr Met Glu Leu Val Gly Trp Leu Val Asp Lys Gly Ile Thr
            225                 230                 235 tcg gag aag cag tgg atc cag gag gac cag gcc tca tac atc tcc ttc    769
Ser Glu Lys Gln Trp Ile Gln Glu Asp Gln Ala Ser Tyr Ile Ser Phe
        240                 245                 250 aat gcg gcc tcc aac tcg cgg tcc caa atc aag gct gcc ttg gac aat    817
Asn Ala Ala Ser Asn Ser Arg Ser Gln Ile Lys Ala Ala Leu Asp Asn
    255                 260                 265 gcg gga aag att atg agc ctg act aaa acc gcc ccc gac tac ctg gtg    865
Ala Gly Lys Ile Met Ser Leu Thr Lys Thr Ala Pro Asp Tyr Leu Val
270                 275                 280                 285 ggc cag cag ccc gtg gag gac att tcc agc aat cgg att tat aaa att    913
Gly Gln Gln Pro Val Glu Asp Ile Ser Ser Asn Arg Ile Tyr Lys Ile
                290                 295                 300 ttg gaa cta aac ggg tac gat ccc caa tat gcg gct tcc gtc ttt ctg    961
Leu Glu Leu Asn Gly Tyr Asp Pro Gln Tyr Ala Ala Ser Val Phe Leu
            305                 310                 315 gga tgg gcc acg aaa aag ttc ggc aag agg aac acc atc tgg ctg ttt   1009
Gly Trp Ala Thr Lys Lys Phe Gly Lys Arg Asn Thr Ile Trp Leu Phe
        320                 325                 330 ggg cct gca act acc ggg aag acc aac atc gcg gag gcc ata gcc cac   1057
Gly Pro Ala Thr Thr Gly Lys Thr Asn Ile Ala Glu Ala Ile Ala His
```

```
            335                 340                 345
act gtg ccc ttc tac ggg tgc gta aac tgg acc aat gag aac ttt ccc    1105
Thr Val Pro Phe Tyr Gly Cys Val Asn Trp Thr Asn Glu Asn Phe Pro
350                 355                 360                 365 ttc aac gac tgt gtc gac aag atg gtg atc tgg tgg gag gag ggg aag    1153
Phe Asn Asp Cys Val Asp Lys Met Val Ile Trp Trp Glu Glu Gly Lys
                370                 375                 380 atg acc gcc aag gtc gtg gag tcg gcc aaa gcc att ctc gga gga agc    1201
Met Thr Ala Lys Val Val Glu Ser Ala Lys Ala Ile Leu Gly Gly Ser
            385                 390                 395 aag gtg cgc gtg gac cag aaa tgc aag tcc tcg gcc cag ata gac ccg    1249
Lys Val Arg Val Asp Gln Lys Cys Lys Ser Ser Ala Gln Ile Asp Pro
        400                 405                 410 act ccc gtg atc gtc acc tcc aac acc aac atg tgc gcc gtg att gac    1297
Thr Pro Val Ile Val Thr Ser Asn Thr Asn Met Cys Ala Val Ile Asp
    415                 420                 425 ggg aac tca acg acc ttc gaa cac cag cag ccg ttg caa gac cgg atg    1345
Gly Asn Ser Thr Thr Phe Glu His Gln Gln Pro Leu Gln Asp Arg Met
430                 435                 440                 445 ttc aaa ttt gaa ctc acc cgc cgt ctg gat cat gac ttt ggg aag gtc    1393
Phe Lys Phe Glu Leu Thr Arg Arg Leu Asp His Asp Phe Gly Lys Val
                450                 455                 460 acc aag cag gaa gtc aaa gac ttt ttc cgg tgg gca aag gat cac gtg    1441
Thr Lys Gln Glu Val Lys Asp Phe Phe Arg Trp Ala Lys Asp His Val
            465                 470                 475 gtt gag gtg gag cat gaa ttc tac gtc aaa aag ggt gga gcc aag aaa    1489
Val Glu Val Glu His Glu Phe Tyr Val Lys Lys Gly Gly Ala Lys Lys
        480                 485                 490 aga ccc gcc ccc agt gac gca gat ata agt gag ccc aaa cgg gtg cgc    1537
Arg Pro Ala Pro Ser Asp Ala Asp Ile Ser Glu Pro Lys Arg Val Arg
    495                 500                 505 gag tca gtt gcg cag cca tcg acg tca gac gcg gaa gct tcg atc aac    1585
Glu Ser Val Ala Gln Pro Ser Thr Ser Asp Ala Glu Ala Ser Ile Asn
510                 515                 520                 525 tac gca gac agg tac caa aac aaa tgt tct cgt cac gtg ggc atg aat    1633
Tyr Ala Asp Arg Tyr Gln Asn Lys Cys Ser Arg His Val Gly Met Asn
                530                 535                 540 ctg atg ctg ttt ccc tgc aga caa tgc gag aga atg aat cag aat tca    1681
Leu Met Leu Phe Pro Cys Arg Gln Cys Glu Arg Met Asn Gln Asn Ser
            545                 550                 555 aat atc tgc ttc act cac gga cag aaa gac tgt tta gag tgc ttt ccc    1729
Asn Ile Cys Phe Thr His Gly Gln Lys Asp Cys Leu Glu Cys Phe Pro
        560                 565                 570 gtg tca gaa tct caa ccc gtt tct gtc gtc aaa aag gcg tat cag aaa    1777
Val Ser Glu Ser Gln Pro Val Ser Val Val Lys Lys Ala Tyr Gln Lys
    575                 580                 585 ctg tgc tac att cat cat atc atg gga aag gtg cca gac gct tgc act    1825
Leu Cys Tyr Ile His His Ile Met Gly Lys Val Pro Asp Ala Cys Thr
590                 595                 600                 605 gcc tgc gat ctg gtc aat gtg gat ttg gat gac tgc atc ttt gaa caa    1873
Ala Cys Asp Leu Val Asn Val Asp Leu Asp Asp Cys Ile Phe Glu Gln
                610                 615                 620 taa                                                                 1876

<210> SEQ ID NO 5
<211> LENGTH: 621
<212> TYPE: PRT
<213> ORGANISM: adeno-associated virus 2

<400> SEQUENCE: 5
```

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
50                      55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
            130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
                195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
            290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415
```

```
Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620

<210> SEQ ID NO 6
<211> LENGTH: 1194
<212> TYPE: DNA
<213> ORGANISM: Artificial
<220> FEATURE:
<223> OTHER INFORMATION: AAV2 Rep52 AcMNPV optimized
<220> FEATURE:
<221> NAME/KEY: misc_feature
<223> OTHER INFORMATION: AcMNPV optimized Rep52 coding sequence

<400> SEQUENCE: 6
atggaattgg tcggttggtt ggtggacaag ggtattacct cggagaagca atggatacaa      60
gaagatcaag cctcatacat ctcgtttaat gcggcatcca actcgcgtag ccaaatcaaa     120
gctgccttgg acaatgcggg caagattatg agcctgacta aaaccgcccc cgactacctg     180
gtgggccagc aacccgtgga agacatttcc agcaatcgca tctataagat tttggagtta     240
aacggctacg atcctcaata tgcggcttcc gtattttttgg ctgggcgac gaaaaagttt     300 ggcaaaagaa acaccatttg ttgtttggaa cctgcaacta cgggaaaaac aaacatagcg     360
gaggccatag cccacactgt accttttat ggctgcgtta actggaccaa tgagaacttt     420
ccattcaacg actgtgtcga caagatggtt atttggtggg aggaaggcaa aatgaccgct     480
aaagtcgtgg agtcggccaa agcaatttta ggaggcagca agtgcgcgt agaccagaaa     540 tgcaaaagct ctgcgcagat agaccccgaca ccggtgatcg ttacaagcaa cacgaacatg     600
tgcgccgtga ttgacggtaa cagtacgaca ttcgaacacc aacaccgtt gcaagaccga     660 atgttcaaat ttgaattgac gcgccgactg gatcatgatt ttggcaaggt aacaaaacaa     720
gaagtcaaag acttctttcg ttgggcaaag gatcacgttg ttgaagtgga acatgaattt     780
tacgtcaaaa aaggtggtgc taagaaaaga cccgccccga gtgatgcaga tataagtgag     840
```

```
cccaaacgag tgagagaatc ggttgcgcag ccaagcacgt cagatgcgga agcttcgata    900
aactacgcag accgctacca aaacaaatgt tctcgtcacg taggcatgaa cttaatgttg    960
tttccctgca gacaatgtga gagaatgaat cagaatagta atatctgttt cactcacggc   1020
cagaaagact gtttagaatg ctttccggtg tcagaatctc aacccgtttc tgtcgtaaaa   1080
aaggcgtatc aaaaattatg ctatattcat catatcatgg gaaaagtgcc agacgcttgt   1140
actgcctgcg atctggttaa tgtggatttg gatgactgta tctttgaaca ataa         1194
```

<210> SEQ ID NO 7
<211> LENGTH: 19
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr59

<400> SEQUENCE: 7

```
aatgggcggt aggcgtgta                                                  19
```

<210> SEQ ID NO 8
<211> LENGTH: 22
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr60

<400> SEQUENCE: 8

```
aggcgatctg acggttcact aa                                              22
```

<210> SEQ ID NO 9
<211> LENGTH: 21
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr180

<400> SEQUENCE: 9

```
cgaaccgatg gctggactat c                                               21
```

<210> SEQ ID NO 10
<211> LENGTH: 23
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr181

<400> SEQUENCE: 10

```
tgctgctaca agatttggca agt                                             23
```

<210> SEQ ID NO 11
<211> LENGTH: 20
<212> TYPE: DNA
<213> ORGANISM: artificial
<220> FEATURE:

<223> OTHER INFORMATION: primer
<220> FEATURE:
<221> NAME/KEY: misc_feature
<223> OTHER INFORMATION: pr340

<400> SEQUENCE: 11
atacaaccgt tggttgcacg                                               20

<210> SEQ ID NO 12
<211> LENGTH: 18
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr341

<400> SEQUENCE: 12
cgggacacgc catgtatt                                                 18

<210> SEQ ID NO 13
<211> LENGTH: 20
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr402

<400> SEQUENCE: 13
gggagtggcg gcgttgattt                                               20

<210> SEQ ID NO 14
<211> LENGTH: 24
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr403

<400> SEQUENCE: 14
gcacagttca agcctcacag ccta                                          24

<210> SEQ ID NO 15
<211> LENGTH: 22
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr404

<400> SEQUENCE: 15
caaacgtggt ttcgtgtgcc aa                                            22

<210> SEQ ID NO 16
<211> LENGTH: 25
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr405

```
<400> SEQUENCE: 16
gatgcatgac ttcacccaca cactt                                            25

<210> SEQ ID NO 17
<211> LENGTH: 25
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr406

<400> SEQUENCE: 17
acagccattg taatgagacg cacaa                                            25

<210> SEQ ID NO 18
<211> LENGTH: 25
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr407

<400> SEQUENCE: 18
cctagcgccc gatcagcaac tatat                                            25

<210> SEQ ID NO 19
<211> LENGTH: 25
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr408

<400> SEQUENCE: 19
taccgactct gctgaagagg aggaa                                            25

<210> SEQ ID NO 20
<211> LENGTH: 23
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr409

<400> SEQUENCE: 20
tgcgtctggt gcaaactcct tta                                              23

<210> SEQ ID NO 21
<211> LENGTH: 22
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr410

<400> SEQUENCE: 21
gattcgtcat ggccaccaca aa                                               22
```

-continued

```
<210> SEQ ID NO 22
<211> LENGTH: 23
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr411

<400> SEQUENCE: 22
ccaaagcgcc cgttgattat ttt                                          23

<210> SEQ ID NO 23
<211> LENGTH: 23
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr412

<400> SEQUENCE: 23
gcgtacttgc ggctgtcgtt gta                                          23

<210> SEQ ID NO 24
<211> LENGTH: 25
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr413

<400> SEQUENCE: 24
cgaggtcaag ttcaaagggc aacat                                        25

<210> SEQ ID NO 25
<211> LENGTH: 24
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr426

<400> SEQUENCE: 25
gcatttcgca gctctccttc aatt                                         24

<210> SEQ ID NO 26
<211> LENGTH: 23
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr427

<400> SEQUENCE: 26
cttcaagcga gaacgcagca att                                          23

<210> SEQ ID NO 27
<211> LENGTH: 20
```

```
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr428

<400> SEQUENCE: 27
gtggcgtttg ccgtggaaaa                                                   20

<210> SEQ ID NO 28
<211> LENGTH: 23
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr429

<400> SEQUENCE: 28
tgcagctgtg cgttttgaat gaa                                               23

<210> SEQ ID NO 29
<211> LENGTH: 22
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr1018

<400> SEQUENCE: 29
ttgttatgtc aatttgtagc gc                                                22

<210> SEQ ID NO 30
<211> LENGTH: 22
<212> TYPE: DNA
<213> ORGANISM: artificial
<220> FEATURE:
<223> OTHER INFORMATION: primer
<220> FEATURE:
<221> NAME/KEY: misc_feature
<223> OTHER INFORMATION: pr1019

<400> SEQUENCE: 30
tgcataaaga cacagtacaa cg                                                22

<210> SEQ ID NO 31
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<223> OTHER INFORMATION: pr1020

<400> SEQUENCE: 31
gacatagttc gtttgaaaat tatccc                                            26

<210> SEQ ID NO 32
<211> LENGTH: 23
<212> TYPE: DNA
<213> ORGANISM: Artificial
<220> FEATURE:
<223> OTHER INFORMATION: primer
```

```
<220> FEATURE:
<221> NAME/KEY: misc_feature
<223> OTHER INFORMATION: pr1021

<400> SEQUENCE: 32
aacgatcaag ctgttaataa acg                                              23

<210> SEQ ID NO 33
<211> LENGTH: 19
<212> TYPE: DNA
<213> ORGANISM: Artificial
<220> FEATURE:
<223> OTHER INFORMATION: primer
<220> FEATURE:
<221> NAME/KEY: misc_feature
<223> OTHER INFORMATION: pr1024

<400> SEQUENCE: 33
cgcttcggcg tagtttacc                                                   19

<210> SEQ ID NO 34
<211> LENGTH: 19
<212> TYPE: DNA
<213> ORGANISM: Artificial
<220> FEATURE:
<223> OTHER INFORMATION: primer
<220> FEATURE:
<221> NAME/KEY: misc_feature
<223> OTHER INFORMATION: pr1025

<400> SEQUENCE: 34
cgctataagc gcgggttac                                                   19
```

DNA IMPURITIES IN A COMPOSITION COMPRISING A PARVOVIRAL VIRION

CROSS-REFERENCE TO RELATED APPLICATIONS

This application is the National Phase of International Patent Application No. PCT/EP2015/077882, filed Nov. 27, 2015, published on Jun. 2, 2016 as WO 2016/083560 A1, which claims priority to European Patent Application No. 14195464.4, filed Nov. 28, 2014. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on May 24, 2017, is named 069818-2980SequenceListing.txt and is 28 KB.

FIELD OF THE INVENTION

The current invention relates to the field of virology and gene therapy. In particular, the invention relates to a method for identifying and/or quantifying an overrepresented nucleic acid impurity in a composition.

BACKGROUND OF THE INVENTION

Recombinant vectors based on adeno associated virus (AAV) have been used in numerous clinical trials and hold a great promise for human gene therapy. The principle characteristics responsible for wide success of rAAV are its ability to establish persistent transgene expression combined with good safety characteristics. Preparation of clinical grade rAAV's is amongst other focused on minimalization of DNA impurities, which potentially may encode oncogenes, antibiotic markers or immunogenic peptides compromising safety of the vector (Wright et al., 2008, Gene Ther. 15, 840-848).

Although, tremendous progress has been made to both upstream and downstream processing of rAAV to ensure the purity of the final product, the complete elimination of unwanted DNA does not seem plausible. The packaging of cellular or helper vector DNA appears to be a byproduct of AAV biology and as such is inherently linked to the encapsidation of the intended transgene DNA. Once unrelated DNA is encapsidated to preformed capsids the particles become undistinguishable from the capsids containing only the intended expression cassette and it is virtually impossible to separate them.

Therefore, in order to support clinical development and understand the risks related to presence of unwanted DNA in rAAV vectors there is a need to evaluate the potential for protein expression from these genetic elements in a range of cell lines that reflect biodistribution profile of the rAAV used, to exclude the theoretic possibility that unintended protein expression, could lead to undesirable effects such e.g. cellular rearrangements, tumorgenicity or unwanted immune responses potentially compromising safety and/or efficacy of the vector.

So far, presence and concentration of DNA impurities contaminating rAAV preparations has been reported in literature (Blouin et al., 2004, J. Gene Med. 6 Suppl 1, S223-S228; Nony et al., 2003, J. Virol. 77, 776-781; Chadeuf et al., 2005, Mol. Ther. 12, 744-753; Wright et al., 2008, supra). The identity of these impurities was traced back to either helper plasmid or host cell DNA (Wright et al., 2008, supra). Only limited number of studies tackled the issue of putative protein expression originating from this co-packaged residual DNA. Wright and coworkers analyzed the expression of cap, amp(r), and two adenoviral genes E2A and E4 by RT-qPCR upon infection of human hepatocytes or mice with rAAV and found no detectable transcription (Hauck et al., 2009, Mol Ther. 17(1) 144-152). On contrary, Miller et al., have found DNA impurity driven expression of cap gene using complementation assay (Halbert et al., 2011, Gene Ther. 18(4): 411-417).

The current method of choice for analysing DNA impurities in biopharmaceutical virion preparations is qPCR. Using this method, the presence and quantity of a specific DNA impurity is determined. Importantly, the skilled person thus selects on forehand the DNA impurity to be detected, i.e. prior to performing a qPCR, as there is a general consensus in the art that DNA impurities are randomly packaged into the virion. Such (preselected) DNA impurity may e.g. comprise host cell DNA, Rep, Cap or plasmid nucleotide sequences. For example, as indicated by Thorne et al (2009, Hum. Gene Ther. 20: 707-714) host cell DNA impurities are monitored using two targets: the human papillomavirus (HPV) E6/E7 transforming genes as the relevant sequence for safety assessment for a HeLa-based production system and the highly expressed, high-copy gene for ribosomal RNA (rRNA) as a sensitive general marker. According to Thorne et al (supra), the most prevalent copackaged sequences are derived from the packaging plasmid, including AAV rep and cap and the bacterial and mammalian cell selection marker genes. Furthermore, Ye et al. (2011, Gene Ther. 18, 135-144) disclose that DNA sequences from the HSV packaging plasmid are packaged randomly during rAAV production in a mammalian cell line. According to Ye et al, the AAV virion comprises random fragments from across the entire HSV genome. In addition, Chadeuf et al (supra) show that in case of a smaller DNA plasmid, the complete plasmid and viral ITRs are encapsulated into the virion, including the selection marker gene. Therefore, there appeared no need to detect specific nucleotide sequences as DNA impurities seemed to be randomly packaged into a parvoviral virion.

In contrast to the general teachings that DNA impurities are randomly packaged into the virion, the present invention shows that some DNA impurities are in fact overrepresented. As a consequence, the currently used methods for detecting a DNA impurity in a biopharmaceutical composition could lead to a drastic underestimation of the DNA impurities present in a composition. Such underestimation of a DNA impurity in a pharmaceutical composition could result in the administration of compositions that are not clinically pure enough, leading to a potential safety health risk for patients.

Therefore, there is a need in the art for means and methods for identifying and quantifying an overrepresented DNA impurity in biological compositions, such as e.g. biopharmaceutical preparations. It is an object of the present invention to provide such means and methods.

SUMMARY OF THE INVENTION

In a first aspect, the present invention relates to a method for identifying and quantifying an overrepresented nucleic acid impurity in a composition comprising a parvoviral vector and wherein the method comprises the steps of:

a) subjecting the composition to nucleic acid sequencing to obtain random reads of nucleotide sequences;
b) comparing the random reads from step a) with a nucleotide sequence of a biological component used in the process for producing the composition whereby a match between a random read and a nucleotide sequence of a biological component identifies a nucleic acid impurity;
c) determining the average number of reads per parvoviral vector; and
d) determining the number of reads per nucleotide of the overrepresented nucleic acid impurity, wherein a nucleic acid impurity is identified as an overrepresented impurity when the distribution of reads is not random and the overrepresented impurity comprises 2, 3, 4, 5, 6, 7, 8, 9, 10, 15, 20 or 50 times the average number of reads of the biological component, or when the number of reads per nucleotide of a nucleic acid impurity is at least 0.001, 0.01, 0.1, 0.2, 0.3, 0.4, 0.5, 0.6, 0.7, 0.8, 0.9, 1.0, 2.0, 3.0, 5.0, 7.0 or 10% of the average number of reads per parvoviral vector.

In a preferred embodiment, the nucleic acid sequencing in step (a) comprises high-throughput sequencing.

In a preferred embodiment, the parvoviral vector is a recombinant adeno-associated virus (rAAV) vector.

In a preferred embodiment, the nucleotide sequence of a biological component is selected from a group consisting of nucleotide sequences of: a host cell, a plasmid, a vector other than the recombinant parvoviral vector and a helper virus, wherein preferably the vector is a baculoviral vector.

In a preferred embodiment, the helper virus is an recombinant adenovirus and/or a recombinant herpes simplex virus.

In a preferred embodiment, the nucleotide sequence of the biological component comprises a nucleotide sequence encoding for Rep, Cap and/or a transgene, wherein preferably the biological component comprises a nucleotide sequence encoding for a transgene, wherein more preferably the biological component comprises a nucleotide sequence encoding for a transgene that is flanked by at least one parvoviral ITR, and wherein most preferably the biological component comprises a nucleotide sequence encoding for a transgene that is flanked by at least one parvoviral ITR on each side.

In a preferred embodiment, the overrepresented nucleic acid impurity is quantified in a second or further composition.

In a second aspect, the present invention relates to a method for quantifying a nucleic acid impurity in a composition comprising a parvoviral vector, wherein the method comprises the step of determining the relative abundance of a nucleic acid impurity, which nucleic acid impurity comprises a nucleotide sequence that is located between 1-8000 bp, 1-5000 bp, 1-3000 bp, 1-1000 bp, 1-500 bp, 1-250 bp or 1-100 bp immediately adjacent of a parvoviral ITR sequence when the ITR sequence is present in a biological component used in a process for producing the composition and wherein the biological component comprises a transgene flanked by at least one copy of the parvoviral ITR sequence.

In a preferred embodiment, the biological component is selected from a group consisting of a host cell, a plasmid, a vector other than the recombinant parvoviral vector and a helper virus, wherein preferably the vector is a baculoviral vector.

In a preferred embodiment, the parvoviral vector is a recombinant adeno-associated virus (rAAV) vector.

In a preferred embodiment, the nucleotide sequence of the nucleic acid impurity is located immediately adjacent on each side of the parvoviral ITR sequence when the ITR sequence is present in a biological component used in a process for producing the composition.

In a preferred embodiment, the relative abundance is determined as compared to a nucleotide sequence of the parvoviral vector, and/or a reference sequence the composition.

In a preferred embodiment, the relative abundance is determined by:
a) the average number of reads per nucleic acid of the nucleic acid impurity as defined above; and
  i) the average number of reads per nucleic acid of the reference sequence; and/or
  ii) the average number of reads per parvoviral vector in the composition; wherein the number of reads is determined by a method as defined above; and/or
b) amplification of the nucleic acid impurity as defined above; and
  i) the reference sequence; and/or
  ii) a nucleotide sequence of a parvoviral vector.

In a preferred embodiment, the relative abundance is determined by Q-PCR and/or by high-throughput sequencing.

In a preferred embodiment, the method further comprises the step of a selective hybridization of an oligonucleotide primer to the nucleic acid impurity as defined above or a complement thereof.

In a preferred embodiment, the oligonucleotide primer selectively hybridizes to a nucleic acid impurity comprising a part of a baculovirus sequence or a complement thereof.

In a third aspect, the present invention relates to a method of determining whether a composition comprising a parvoviral vector is regarded clinically pure, wherein the method comprises the steps of:
  i) quantifying a nucleic acid impurity in a parvoviral vector composition as defined above; and
  ii) determining the composition as being clinically pure if the nucleic acid impurity as defined above is at least 10, 100, 250, 1000 times less present as the reference sequence and/or transgene as determined by the relative abundance of the nucleic acid impurity.

In a preferred embodiment, the composition comprising the parvoviral vector is a pharmaceutical composition. Alternatively, or in combination with another preferred embodiment, in a preferred embodiment of the present invention the composition comprising the parvoviral vector comprises a parvoviral capsid wherein the parvoviral vector is packaged. Alternatively, or in combination with another preferred embodiment, in a preferred embodiment of the present invention the composition comprising the parvoviral vector does not comprise a sample obtained or obtainable from a mammal, wherein the mammal preferably is a non human primate.

DESCRIPTION OF THE INVENTION

The current invention relates to the discovery that DNA impurities are not randomly packaged into parvoviral virion. Instead, there are nucleic acid impurities that are overrepresented in the virion composition. Therefore in a first aspect, the invention relates to a method for identifying a nucleic acid impurity in a composition. Preferably, the composition comprises a parvoviral vector. The method preferably comprises the steps of: a) subjecting the composition to nucleic acid sequencing to obtain random reads of nucleotide sequences; b) comparing the random reads from step a) with a nucleotide sequence of a biological component used in the process for producing the composition, whereby a match between a random read and a nucleotide sequence of a biological component identifies a nucleic acid impurity. For quantifying an identified nucleic acid impurity the method further preferably comprises the steps of: c) determining the average number of reads per parvoviral vector; and d) determining the number of reads per nucleotide of an identified nucleic acid impurity, wherein a nucleic acid impurity is identified as an overrepresented impurity when the distribution of reads is not random and the overrepresented impurity has 2, 3, 4, 5, 6, 7, 8, 9, 10, 15, 20 or 50 times the average number of reads of the biological component, or when the number of reads per nucleotide of a nucleic acid impurity is at least 0.001, 0.01, 0.1, 0.2, 0.3, 0.4, 0.5, 0.6, 0.7, 0.8, 0.9, 1.0, 2.0, 3.0, 5.0, 7.0 or 10% of the average number of reads per parvoviral vector.

The method of the invention thus relates to the identification and quantification of a nucleic acid impurity in a composition. The nucleic acid impurity can be a DNA impurity and/or an RNA impurity, preferably the nucleic acid impurity is a DNA impurity.

The term "nucleic acid impurity" is understood to include any nucleic acid sequence that is not intended to be packaged into the parvoviral virion, such as e.g. nucleotide sequences of a biological component used in the process for producing the composition. In particular, a sequence that is not flanked by one parvoviral ITR on each side may constitute a nucleic acid impurity.

A "parvoviral vector" herein refers to a recombinant nucleic acid molecule comprising one or more polynucleotide sequences of interest (e.g. an expression construct for a gene encoding a product of interest, i.e. a "transgene") that are flanked by at least one (and usually two) parvoviral inverted terminal repeat sequence(s) (ITRs).

A "random distribution of reads" is herein defined as a distribution of reads that align equally over the length of a nucleotide sequence of a biological component used in the process for producing the composition. In particular, a random distribution of reads is defined as a distribution of reads that align equally over the length of a nucleotide sequence of one biological component used in the process for producing the composition. More preferably, the random distribution of reads is herein defined as a distribution of reads that align equally over the length of a nucleotide sequence selected from a group consisting of nucleotide sequences of: a host cell, a plasmid, a vector other than a recombinant parvoviral vector and helper virus, wherein preferably the vector is a baculoviral vector. Therefore, most preferably a random distribution of reads is defined in the invention as a distribution of reads that align equally over the length of a nucleotide sequence of a baculoviral vector.

An equal alignment is herein defined as an equal probability that a read aligns to a specific region of a nucleotide sequence as compared to any other region of the same nucleotide sequence. Preferably, in an equal alignment the number of reads that align to a nucleotide does not deviate more than 0.1, 0.2, 0.5, 1.0, 2.0, 5.0, 10, 15 or 20% of the average number of reads aligning to that nucleotide sequence.

A "non-random distribution of reads" is herein defined as a distribution of reads that do not align equally over the length of a nucleotide sequence of a biological component used in the process for producing the composition. In particular, a non-random distribution of reads is defined as a distribution of reads that do not align equally over the length of a nucleotide sequence of one biological component used in the process for producing the composition. More preferably, a non-random distribution of reads is herein defined as a distribution of reads that do not align equally over the length of a nucleotide sequence selected from a group consisting of nucleotide sequences of: a host cell, a plasmid, a vector other than a recombinant parvoviral vector and helper virus, wherein preferably the vector is a baculoviral vector. Therefore, most preferably a non-random distribution of reads is defined in the invention as a distribution of reads that do not align equally over the length of a nucleotide sequence of a baculoviral vector, i.e. meaning that more reads align to specific regions of the baculoviral vector in comparison to other regions of the baculoviral vector.

Preferably the composition is a composition comprising a (recombinant) parvoviral virion comprising or consisting of (at least) a parvoviral capsid wherein the recombinant parvoviral vector is packaged. The composition and its constituents are further preferably as defined herein below.

In a preferred embodiment of the invention, the method is for identifying and/or quantifaction of nucleic acid impurities that are packaged into a parvoviral virion, i.e. encapsulated within the virion. In particular, the nucleic acid impurity according to the invention is not degraded after nuclease treatment (e.g. RNAse or DNAse treatment) of the composition comprising a parvoviral virion.

Compositions

In a preferred embodiment, a parvoviral vector is contained in a composition. Preferably, the composition is a pharmaceutical composition. The pharmaceutical composition further preferably comprises a pharmaceutically acceptable carrier. Any suitable pharmaceutically acceptable carrier or excipient can be used in the present compositions (See e.g., Remington: The Science and Practice of Pharmacy, Alfonso R. Gennaro (Editor) Mack Publishing Company, April 1997).

Preferred pharmaceutical forms would be in combination with sterile saline, dextrose solution, or buffered solution, or other pharmaceutically acceptable sterile fluids. Alternatively, a solid carrier, may be used such as, for example, microcarrier beads.

Alternatively, or in combination with another preferred embodiment, in a preferred embodiment of the present invention the composition comprising the parvoviral vector does not comprise a sample, such as for example a liver or a muscle sample, obtained or obtainable from a mammal. In an even more preferred embodiment, the composition does not comprise a sample obtained or obtainable from a non-human primate. In a more preferred embodiment, the composition does not comprise genomic DNA from muscle or liver from a mammal, such as for example from a non-human primate.

Nucleic Acid Sequencing

In a method according to the invention, an overrepresented nucleic acid impurity in a composition is identified and quantified. Methods for identifying and quantifying an overrepresented nucleic acid impurity include, but are not limited to, Sanger sequencing or high-throughput sequencing.

In a first embodiment, parvoviral vector DNA may be cloned into a plasmid, followed by conventional Sanger sequencing. Sanger sequencing is herein defined as a method of DNA sequencing that is based on the selective incorporation of chain-terminating dideoxynucleotides by DNA polymerase during in vitro DNA replication. Sanger sequencing according to the current invention comprises so-called chain-terminator Sanger sequencing and/or Dye-terminator Sanger sequencing. Preferably, the Sanger sequencing is dye-terminator Sanger sequencing. Dye-terminator sequencing utilizes labeling of the chain terminator ddNTPs. In particular, in dye-terminator sequencing each of the four dideoxynucleotide chain terminators is labeled with fluorescent dyes, each of which emit light at different wavelengths, which permits sequencing in a single reaction. Other DNA sequencing methods might be equally suitable, such as nanopore DNA sequencing, tunneling currents DNA sequencing, sequencing by hybridization, sequencing with mass spectrometry, microfluidic Sanger sequencing, microscopy-based techniques and RNAP sequencing.

In a preferred embodiment of the current invention, the nucleic acid sequencing comprises high-throughput sequencing. High-throughput sequencing (also referred to as next generation sequencing or deep-sequencing) refers to non-Sanger-based high-throughput DNA sequencing technologies. Thousands, millions or even billions of DNA strands can be sequenced in parallel, yielding substantially more throughput and minimizing the need for the fragment-cloning methods that are often used in Sanger sequencing of genomes.

In a preferred method according to the invention, the high-throughput sequencing comprises Heliscope single molecule sequencing, Single molecule real time (SMRT) sequencing, Ion Torrent sequencing (ion semiconductor), 454 sequencing (pyrosequencing, Roche 454 Life Sciences™, Branford, Conn.), SOLEXA® (sequencing by synthesis, Illumina, Inc, San Diego, Calif.) and/or SOLiD sequencing (sequencing by ligation, ABI, Applied Biosystems, Indianapolis, Ind.). In a further preferred embodiment of the invention, the nucleic acid sequencing comprises SOLiD, SOLEXA® and/or 454 sequencing. In a most preferred embodiment, the nucleic acid sequencing comprises SOLEXA®/Illumina or 454 sequencing.

The method according to the invention is not limited to the currently known high-throughput sequencing methods. In particular, it is understood that novel high-throughput sequencing methods will be developed over time that are equally suitable for use in a method of the invention. In particular, any sequencing method that classifies as a high-throughput sequencing method, i.e. any method that generates thousands, millions or billions of reads in a single run, can be used in a method according to the invention.

In a preferred method according to the invention random reads are obtained by subjecting a composition comprising a parvoviral vector to nucleic acid sequencing. A (sequencing) "read" or "count" is herein defined as an individual string of bases produced during a nucleic acid sequencing method. Different high-throughput sequencing methods can generate different number of reads per run (reaction) and reads of different lengths. For example, Illumina generates up to 3 billion reads per run and a read has an average length of 50-300 bp. On the other hand, 454 sequencing generates about 1 million reads per run with reads having an average length of about 700 bp. The read number (number of reads per run) and read length (number of bases per read) can vary per sequencing run and the read length as well as the read number per run is expected to increase following further development of the different high-throughput sequencing methods.

Identifying an Overrepresented Nucleic Acid Impurity

In an embodiment of the invention, the random reads obtained as described above are compared with a nucleotide sequence of a biological component used in the process for producing the composition, wherein the comparison of random reads to the nucleotide sequence from the biological component results in the identification of the overrepresented nucleic acid impurity. This nucleotide sequence of a biological component may be a suspected or an unsuspected source of nucleotide sequences.

A suspected source of nucleotide sequences may be selected from a group consisting of nucleotide sequences of: a host cell, a plasmid, a vector and a helper virus. Preferably wherein the helper virus is an adenovirus and/or a herpes simplex virus and/or wherein the vector is a baculoviral vector. In a preferred embodiment, the suspected source of nucleotide sequences is a baculoviral vector. In a method according to the invention, the random reads are thus aligned or compared to a suspected source of nucleotide sequences, which leads to the identification of the overrepresented nucleic acid impurity.

Alternatively or in combination with the previous embodiments, the source of nucleotide sequences is an unsuspected source of nucleotide sequences, i.e. the source of nucleotide sequences is not predetermined. The unsuspected source of nucleotide sequences can be retrieved by de novo assembly of the random reads obtained according to the method of the invention and comparing these assembled nucleotide sequences to a nucleotide sequence database. Such nucleotide sequence database may be a privately or publicly available nucleotide sequence database. Examples of a publicly available nucleotide sequence database include, but are not limited to, UCSC Genome Bioinformatics, GenBank, DDBJ, ENA, etc. Comparing the assembled sequence to a sequence in the privately or publicly available database could lead to the identification of the nucleic acid impurity.

In a preferred method of the invention, the nucleotide sequence of a biological component used in the process for producing the composition is a suspected source of nucleotide sequences. In particular, in a preferred embodiment the nucleotide sequence of a biological component is selected from a group consisting of nucleotide sequences of: a host cell, a plasmid, a vector other than the recombinant parvoviral vector and a helper virus. In particular, the nucleotide sequence of the biological component does not comprise a nucleotide sequence of a parvoviral vector.

A host cell according to the present invention can be any cell used in the process for producing the composition. A host cell could be selected from a group consisting of: a plant cell, a bacterial cell, a yeast cell and an animal cell. Preferably, the host cell is an animal cell, and more preferably the host cell is a mammalian host cell or an insect host cell. In a most preferred embodiment of the invention, the host cell is an insect host cell. A nucleotide sequence of a host cell used in the process for producing the composition comprises genomic DNA and/or mitochondrial DNA. Preferably the nucleotide sequence of the host cell comprises genomic DNA. The genomic DNA might comprise a gene selected from a group of genes consisting of: a transgene, a gene encoding Rep, a gene encoding Cap and a gene encoding for a protein or an RNA with a helper function for producing the composition. Such gene encoding for a protein or RNA with a helper function for producing the composition may be derived from an animal virus, such as an adenovirus and/or a herpes simplex virus or an insect virus, such as baculovirus. Alternatively or in combination, the genomic DNA may comprise an ITR sequence. In a preferred embodiment, the genomic DNA of the host cell comprises a transgene flanked by at least one ITR, and preferably the transgene is flanked by an ITR on each side.

A plasmid according to the present invention can be any plasmid used in the process for producing the composition. The plasmid preferably comprises a gene selected from a group of genes consisting of: a resistance gene, a transgene, a gene encoding Rep, a gene encoding Cap and a gene encoding a protein or an RNA with a helper function for producing the composition. Alternatively or in combination, the plasmid may comprise an ITR sequence. In a preferred embodiment, the plasmid comprises a transgene flanked by at least one ITR, and preferably the transgene is flanked by an ITR on each side.

A vector according to the present invention can be any vector used in the process for producing the composition. A vector may be selected from a group consisting of: a plasmid, a viral vector, a cosmid and an artificial chromosome. In a preferred embodiment of the invention, the vector is a viral vector. In the most preferred embodiment, the vector is a baculoviral vector. The baculoviral vector used in a process for producing the composition may comprise a gene selected from a group of genes consisting of: a transgene, a gene encoding Rep, a gene encoding Cap and a gene encoding a protein with a helper function for producing the composition. Alternatively or in combination, the baculoviral vector may comprise an ITR sequence. In a preferred embodiment, the baculoviral vector comprises a transgene flanked by at least one ITR, and preferably the transgene is flanked by an ITR on each side.

A helper virus according to the present invention can be any virus used in the process for producing the composition. In a preferred embodiment, the helper virus is used in a process for producing a parvoviral virion. In a further preferred embodiment, the helper virus is used in a process for producing an recombinant adeno-associated virion (rAAV). In the more preferred embodiment, the helper virus is an adenovirus and/or a herpes simplex virus. In a most preferred embodiment, the helper virus is a recombinant adenovirus and/or a recombinant herpes simplex virus. In a further embodiment, the helper virus comprises a gene selected from a group of genes consisting of: a transgene, a gene encoding Rep, a gene encoding Cap and a gene encoding a protein with a helper function for producing the composition. Alternatively or in combination, the helper virus may comprise an ITR sequence. In a preferred embodiment, the helper virus comprises a transgene flanked by at least one ITR, and preferably the transgene is flanked by an ITR on each side.

In a preferred embodiment, the nucleotide sequence of a biological component used in the process for producing the composition is from a baculoviral vector. In a most preferred embodiment, the nucleotide sequence from a biological component is from a baculoviral vector comprising a transgene, flanked by at least one ITR, and preferably the transgene is flanked by two ITRs.

In combination or alternatively to the above, the nucleotide sequence of the biological component comprises a nucleotide sequence encoding for Rep, Cap and/or a transgene, wherein preferably the biological component comprises a nucleotide sequence encoding for a transgene, wherein more preferably the biological component comprises a nucleotide sequence encoding for a transgene that is flanked by at least one parvoviral ITR, and wherein most preferably the biological component comprises a nucleotide sequence encoding for a transgene that is flanked by at least one parvoviral ITR on each side.

Quantifying an Overrepresented Nucleic Acid Impurity Using Nucleic Acid Sequencing The current invention discloses a method for identifying and quantifying an overrepresented nucleic acid impurity in a composition, wherein the method comprises a step of subjecting the composition to nucleic acid sequencing to obtain random reads of nucleotide sequences. The nucleic acid impurity may be identified as indicated above. The identified nucleic acid impurity may subsequently be quantified by determining the number of reads per nucleic acid of the overrepresented nucleic acid impurity in the composition.

The number of reads per nucleic acid is herein defined as the number of reads that align to a specific nucleic acid of a nucleotide sequence. Thus, the number of reads per nucleic acid of a nucleic acid impurity in the composition is understood as the number of reads that specifically align to a nucleic acid of a nucleic acid impurity.

The number of reads aligning to a specific nucleic acid of a nucleotide sequence translates into the frequency wherein this particular nucleic acid is present in a composition. Thus a high number of reads aligning to a specific nucleic acid is understood as a nucleic acid that is abundant in the composition. Alternatively, if only a few reads align to a specific nucleic acid, it is understood that the presence of that nucleic acid is scarce in the composition.

According to a method of the present invention, a nucleic acid impurity is overrepresented when the distribution of reads is not random and the overrepresented impurity comprises 2, 3, 4, 5, 6, 7, 8, 9, 10, 15, 20 or 50 times the average number of reads of the biological component, or when the number of reads per nucleic acid of a nucleic acid impurity is at least 0.0005, 0.001, 0.002, 0.003, 0.004, 0.005, 0.006, 0.007, 0.008, 0.009, 0.01, 0.02, 0.03, 0.04, 0.05, 0.05, 0.06, 0.07, 0.08, 0.09 0.1, 0.2, 0.3, 0.4, 0.5, 0.6, 0.7, 0.8, 0.9, 1.0, 1.5, 2.0, 3.0, 4.0, 5.0, 6.0, 7.0 or 10% of the average number of reads per nucleic acid of the parvoviral vector.

The average number of reads per parvoviral vector is herein defined as the total number of reads that align to the parvoviral vector divided by the total number of nucleotides of the parvoviral vector. Preferably, the reads and nucleotides of the 25, 50, 75, 100, 200, 300, 400 or 500 most upstream nucleotides of the parvoviral vector and/or the reads and nucleotides of the 25, 50, 75, 100, 200, 300, 400 or 500 most downstream nucleotides of the parvoviral vector are not considered when determining the average number of reads per parvoviral vector. These reads might not be representative for the average number of reads per parvoviral vector as there is an artificial decrease in number of reads that align the most upstream and/or most downstream nucleotides of the parvoviral vector, i.e. at the termini of the vector.

The average number of reads of a biological component is herein defined as the total number of reads that align to a biological component divided by the total number of nucleotides of the biological component. The biological component may comprise one biological component used in the process for producing the composition. More preferably, the biological component is selected from a group consisting of nucleotide sequences of: a host cell, a plasmid, a vector other than a recombinant parvoviral vector and helper virus, wherein preferably the vector is a baculoviral vector. Most preferably, the biological component is a baculoviral vector.

In one embodiment of the present invention, the number of nucleotides of the parvoviral vector may comprise the complete nucleotide sequence of the parvoviral vector, e.g. including the ITR sequences, promoter sequences, a transgene sequence, and any other sequences between the left-ITR and the right-ITR. In a more preferred embodiment, a part of the nucleotide sequence of the parvoviral vector is selected to determine the average number of reads of the parvoviral vector. Such a part of the parvoviral vector may comprise the ITR nucleotide sequence, the promoter sequence and/or the transgene sequence. In a most preferred embodiment, the sequence of a transgene is selected to determine the average number of reads per nucleic acid of the parvoviral vector, i.e. the number of reads aligning to the transgene is divided by the number of nucleotides of the nucleotide sequence of the transgene.

In another embodiment of the current invention, the overrepresented nucleic acid impurity is quantified in a second or further composition. After identifying and quantifying an overrepresented nucleic acid impurity in a first composition, the overrepresented nucleic acid impurity may be subsequently quantified in a further composition. The quantification of an overrepresented nucleic acid impurity in a second or further composition may be determined as outlined above. Alternatively, the quantification of an overrepresented nucleic acid impurity in a second or further composition could be determined by any other method suitable for determining the quantity of the a nucleic acid impurity. Methods for quantifying specific DNA fragments are well-known in the art and equally apply for quantifying an overrepresented nucleic acid impurity in a second or further composition. These methods include, but are not limited to, high-throughput sequencing, Q-PCR, limited-cycle PCR, a hybridization assay, a micro-array and an agarose electrophoresis.

Parvoviral Virions

In a preferred embodiment of the invention, the composition comprises a parvoviral vector. In particular, in a preferred method according to the invention the parvoviral vector is a recombinant adeno-associated virus (rAAV) vector. Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require co-infection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild-type (wt) AAV infection in mammalian cells the Rep genes (i.e. Rep78 and Rep52) are expressed from the P5 promoter and the P19 promoter, respectively and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

A "parvoviral or AAV vector" (or "rAAV vector") herein refers to a nucleic acid molecule comprising one or more polynucleotide sequences of interest (e.g. an expression construct for a gene encoding a product of interest, i.e. a "transgene") that are flanked by at least one parvoviral or AAV inverted terminal repeat sequence (ITRs). Such rAAV vectors can be replicated and packaged into infectious virions when present in a host cell that is expressing AAV rep and cap gene products (i.e. AAV Rep and Cap proteins). A parvoviral or AAV vector preferably is a recombinant nucleic acid molecule, i.e. a nucleic acid molecule that does not occur in nature and is composed by combining sequence elements that do not naturally occur in this combination and/or order.

When an rAAV vector is incorporated into a larger nucleic acid construct (e.g. in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions.

Preferably, a gene product of interest is flanked by AAV ITRs on either side. Any AAV ITR may be used in the method of the invention, including ITRs from AAV1, AAV2, AAV4, AAV5, AAV6, AAV8, AAV9 and/or AAVrh10. ITRs of AAV2 are most preferred. Examples of preferred ITR sequences for use in preferred nucleic acid constructs of the invention are given in SEQ ID NO: 1 (left or upstream ITR) and SEQ ID NO: 2 (right or downstream ITR).

AAV is able to infect a number of mammalian cells. See, e.g., Tratschin et al. (1985, Mol. Cell Biol. 5:3251-3260) and Grimm et al. (1999, Hum. Gene Ther. 10:2445-2450). However, AAV transduction of human synovial fibroblasts is significantly more efficient than in similar murine cells, Jennings et al., Arthritis Res, 3:1 (2001), and the cellular tropicity of AAV differs among serotypes. See, e.g. Goncalves, 2005, Virol J. 2(1):43 who discusses approaches to modification of AAV tropism.

An rAAV vector for use in a method of the present invention may be produced either in mammalian cells or in insect cells. Both methods are described in the art. For example Grimm et al. (2003 Molecular Therapy 7(6):839-850) disclose a strategy to produce AAV vectors in a helper virus free and optically controllable manner, which is based on transfection of only two plasmids into 293T cells. They disclose a method for production of a hybrid AAV vector comprising AAV2 Rep proteins, AAV2 ITRs and AAV5 capsid proteins. This reference is herein included in its entirety. Further information can also be found in Blits et al. (2010) (Journal of Neuroscience methods 185(2):257-263).

The terms "hybrid" and "pseudotyped" are used interchangeably herein and are used to indicate vectors of which the Rep proteins, ITRs and/or capsid proteins are of different serotypes. For example, the ITRs and the Rep proteins are of AAV2 and the capsid proteins are of AAV5. The term "chimeric" is used herein to describe that a single gene, such as for example the capsid, is composed of at least two sequences derived from different serotypes.

AAV Production Methods

An rAAV vector in a composition according to the present invention may be produced using a classical production method for rAAV. Such classical production methods are based on transient transfection protocols of target/producer cells (Merten et al, Gene Ther, 2006, 12: S51-S61). This is a trans-complementation and transitory transfection based approach, which requires the following genetic elements: (i) the sequence of the rAAV genome. The sequence of the rAAV genome can be cloned into a plasmid (the so-called viral vector plasmid). This viral vector plasmid usually comprises at least one ITR and an expression cassette for the expression of a transgene; (ii) the sequence encoding rep and cap, and (iii) the required helper functions encoded by a natural auxiliary virus, such as an adenovirus and/or an herpes simplex virus.

For example, rAAVs can be produced in mammalian cells according to the following method, but is not limited thereto: The vector genome contains the transgene expression cassette flanked by two inverted terminal repeats (ITRs) derived from AAV serotype 2. The total length of the viral vector genome may not exceed the wild type genome size of 4.7 kB in order to maintain efficient packaging efficiency. A single capsid is composed of 60 viral proteins of either, VP1 (62 kDa), VP2 (73 kDa), or VP3 (87 kDa), at a ratio of 1:1:10. The manufacturing process of AAV vectors is based upon Ca(PO4)2 transfection of two plasmids into human embryonic kidney production cells (HEK293) in roller bottles (850 $cm^2$ surface area) followed by purification of the encapsidated vector genomes by filtration and chromatography techniques. The first plasmid is the viral vector plasmid and contains an expression construct which is flanked by AAV2 ITRs. The second plasmid is the packaging plasmid and encodes the AAV rep type 2 and cap type 5 genes of the desired serotype and adenovirus early helper genes E2A, VA, E4 (pDP5; nucleotide sequence disclosed in SEQ ID NO:3). The genome of the production cell line comprises the adenovirus E1 to provide helper functions. Following co-transfection with the two plasmids in Iscove's Modified Dulbecco's Medium (IMDM) containing 10% fetal calf serum (FCS), the cells are incubated for three days in serum-free Dulbecco's modified Eagle's medium (DMEM) to allow vector production to occur. Vector production in roller bottles on average results in yields of $3\times10^3$ vector genomes per cell or $4\times10^{11}$ vector genomes per roller bottle (quantified by qPCR). Subsequently, the cell culture is lysed by a buffer containing Triton-X-100 and cell debris removed by low speed centrifugation. The clarified bulk is purified by AVB Sepharose affinity chromatography and formulated into PBS/5% Sucrose by concentration and diafiltration using a 400 kDa hollow fiber module (for example from Spectrum Laboratories).

Alternatively, a rAAV in a composition according to the present invention may be produced in a predominantly transfection-independent method. Such methods could be based either on the use of packaging/producer cell lines, which produce rAAV after induction, or on the use of the baculovirus/insect cell system.

Packaging cells can harbour a part of all the necessary AAV genetic elements, such as the AAV helper sequences rep and cap. Subsequent induction of the rAAV production from a packaging cell line could be carried out by transfection of a plasmid containing the rAAV sequence (the viral vector plasmid) followed by the introduction of a sequence encoding the required helper functions, such as an infection with (replication defective) adenovirus or herpes simplex virus. Producer cell lines can be complete trans-complementing systems, which harbour all necessary AAV derived components integrated their genome, that is, AAV helper sequences (rep-cap) together with the viral vector sequence. Induction of rAAV production can occur after the introduction of a sequence encoding the required helper functions.

On the other hand, the sequence of the rAAV genome, comprising at least one ITR and a expression cassette for the expression of a transgene, may be embedded in the genome of a helper virus, such as the adenovirus or herpes simplex virus, respectively generating a rAAV/Ad-hybrid system (Thorne et al., 2009; Hum. Gene Ther. 20; 707-714) or rAAV/HSV-hybrid system (Clement et al., 2009; Hum. Gene ther. 20; 796-806; Ye et al., 2014; Hum. Gene Ther. 15; 1-6).

Alternatively, an AAV vector for use in a method of the present invention may be produced in insect cells, as has been described previously by Urabe et al. (Journal of Virology 2006 80(4):1874-1885). In this system, the sequence of the rAAV genome may be cloned into a recombinant baculovirus.

The DNA impurities in a composition comprising a parvoviral vector may derive from any biological component used in the process for producing the composition. The composition may be produced according to any of the methods as outlined above.

Preferably, in a method according to the present invention the nucleotide sequence of a biological component is selected from a group consisting of nucleotide sequences of: a host cell, a plasmid, a vector and a helper virus. In a preferred embodiment, the biological component comprises at least one of the following genetic elements: (i) the sequence of the rAAV genome, preferably comprising at least one ITR and an expression cassette for the expression of a transgene; (ii) a sequence encoding rep and/or cap, and/or (iii) a sequence encoding the required helper functions, which are naturally encoded by an auxiliary virus, such as an adenovirus and/or an herpes simplex virus. More preferably, the biological component comprises at least one ITR and an expression cassette for the expression of a transgene.

In a preferred method according to the invention, the vector is a baculoviral vector. The Baculoviridae are a family of large, enveloped DNA viruses. Baculoviruses infect preferentially arthropod with the vast majorities of permissive species falling within the order of Lepidoptera. Several continuous cell lines such as Sf9, Sf21 or High Five allowing in vitro baculovirus propagation are commercially available and can be used for the production of a composition according to the present invention.

Recombinant baculoviruses derived from Autographa californica multinuclear polyhedrosis virus (AcMNPV) are the most commonly used in biotechnology, in particular for the production of recombinant proteins or of virus like particles (VLP ie shells devoid of viral nucleic acids).

Main advantages of production based on the baculovirus expression vector system (BEVS) can be summed up as following: (i) the presence of very strong promoters (polyhedrine or p10) enable the production of high quantity of heterologous proteins without gene size limitation; (ii) the insect cells possess the ability to perform the main post-translational modifications, thereby allowing the production of biologically active proteins; and (iii) the baculovirus technology can be easily implemented, scale-up is readily achievable, cells are grown in suspension, and various serum-free media are commercially available.

Assembling viral particles is a more complex process than expressing a single protein. However, it has shown that VLP based on HBV, B19 parvovirus, rotavirus, human papillomavirus could be successfully produced with the BEVS. Furthermore, a baculovirus expression vector system can be used for the production of rAAV (Merten et al, supra, Urabe et al., 2002).

Therefore, in the method of the invention, a parvoviral virion may be produced using a baculovirus expression vector system in mammalian cells or in insect cells. Preferably, the parvoviral virion is produced using a baculovirus expression vector system in insect cells.

In a preferred embodiment of the invention, the baculoviral vector comprises a nucleotide sequence encoding for Rep, Cap and/or a transgene, wherein preferably the baculoviral vector comprises a nucleotide sequence encoding for a transgene, wherein more preferably the baculoviral vector comprises a nucleotide sequence encoding for a transgene that is flanked by at least one parvoviral ITR, and wherein most preferably the baculoviral vector comprises a nucleotide sequence encoding for a transgene that is flanked by at least one parvoviral ITR on each side.

Also modifications in the Rep and VP1, VP2 and VP3 sequences previously disclosed can be employed in the present invention, such as for example disclosed in international publications WO 2007/046703, WO 2007/148971, WO 2009/014445, WO 2009/104964 and/or WO 2011/112089.

AAV ITR and Rep sequences that may be used in a method of the present invention for the production of rAAV vectors can be derived from the genome of any AAV serotype. Generally, the AAV serotypes have genomic sequences of significant homology at the amino acid and the nucleic acid levels. This provides an identical set of genetic functions to produce virions which are essentially physically and functionally equivalent. For the genomic sequence of the various AAV serotypes and an overview of the genomic similarities see e.g. GenBank Accession number U89790; GenBank Accession number J01901; GenBank Accession number AF043303; GenBank Accession number AF085716; Chiorini et al. (1997, J. Vir. 71: 6823-33); Srivastava et al. (1983, J. Vir. 45:555-64); Chiorini et al. (1999, J. Vir. 73:1309-1319); Rutledge et al. (1998, J. Vir. 72:309-319); and Wu et al. (2000, J. Vir. 74: 8635-47). rAAV serotypes 1, 2, 3, 4, 5, 6, 7, 8, 9, 10, 11 and 12 can be used as a source of AAV nucleotide sequences for use in context of the present invention. rAAV serotypes 1, 2, 3, 4 and 5 are preferred source of AAV nucleotide sequences. Preferably the AAV ITR sequences in the context of the present invention are derived from AAV1, AAV2, and/or AAV5. More preferably, the ITR sequences in a method of the present invention are AAV2 ITR. Likewise, the Rep (Rep78/68 and Rep52/40) coding sequences are preferably derived from AAV1, AAV2, and/or AAV5, more preferably AAV2

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al., 1999, J. Virol., 73(2):939-947). Moreover, the Rep sequences and ITRs of many AAV serotypes are known to efficiently cross-complement (i.e., functionally substitute) corresponding sequences from other serotypes in production of AAV particles in mammalian cells. US2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. In a preferred embodiment, the rAAV vector comprises VP1 proteins. The ability of Rep and ITR sequences to cross-complement corresponding sequences of other serotypes allows for the production of pseudotyped rAAV particles comprising the capsid proteins of one serotype (e.g., AAV5) and the Rep and/or ITR sequences of another AAV serotype (e.g., AAV2). Such pseudotyped rAAV particles are a part of the method of the present invention. Herein, a pseudotyped rAAV particle may be referred to as being of the type "x/y", where "x" indicates the source of ITRs and "y" indicates the serotype of capsid, for example a 2/5 rAAV particle has ITRs from AAV2 and a capsid from AAV5.

Modified "AAV" sequences also can be used in the context of the present invention, e.g. for the production of rAAV vectors in insect cells. Such modified sequences e.g. include sequences having at least about 70%, at least about 75%, at least about 80%, at least about 85%, at least about 90%, at least about 95%, or more nucleotide and/or amino acid sequence identity (e.g., a sequence having from about 75% to about 99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

ITR, Rep and Cap sequences can be modified as desired to obtain efficient production of rAAV or pseudotyped rAAV vectors in cells, such as insect cells. E.g., the start codon of the Rep sequences can be modified, VP splice sites can be modified or eliminated, and/or the VP1 start codon can be modified to improve the production of rAAV vectors in the (insect) cell, as is for example disclosed in WO 2007/046703, WO 2007/148971 and/or, WO 2009/014445. Also included in the present invention are chimeric AAV capsids, wherein for example VP1 of AAV5 is partially or fully replaced by VP1 derived of AAV2 and VP2 and 3 are derived of AAV5 (Urabe et al., 2006; WO2000/028004). Preferred adenoviral vectors are modified to reduce the host response as reviewed by Russell (2000, J. Gen. Virol. 81: 2573-2604), or as described in US20080008690 and by Zaldumbide and Hoeben (Gene Therapy 2008:239-246).

Preferably an AAV Rep protein comprised within a gene therapy vector according to the present invention is an AAV serotype 2 Rep protein. Even more preferably, a Rep78 protein having the nucleic acid sequence of SEQ ID NO: 4 and/or an amino acid sequence according to SEQ ID NO: 5 is employed in the present invention and a Rep52 protein having the nucleic acid sequence of SEQ ID NO: 6 is employed in the present invention.

Quantifying an Overrepresented Nucleic Acid Impurity

Alternatively or in combination with any of the embodiments as described above, the current invention further relates to the quantification of an overrepresented nucleic acid impurity. In particular, the current invention relates to the discovery that specific DNA impurities are overrepresented in a composition comprising a parvoviral vector. These DNA impurities comprise nucleotide sequences that immediately flank the ITRs of a parvoviral nucleotide sequence during the production process of a parvoviral virion. Thus for example, sequences upstream of a left parvoviral ITR and/or sequences downstream of a right parvoviral ITR are overrepresented in the parvoviral virion.

Thus in another aspect, the invention relates to a method for quantifying a nucleic acid impurity in a composition comprising a parvoviral vector, wherein the method comprises the step of determining the relative abundance of a nucleic acid impurity, which nucleic acid impurity comprises a nucleotide sequence that is located between 1-8000 bp, 1-5000 bp, 1-3000 bp, 1-1000 bp, 1-500 bp, 1-250 bp or 1-100 bp immediately adjacent of an parvoviral ITR sequence when the ITR sequence is present in a biological component used in a process for producing the composition and wherein the biological component comprises a transgene flanked by at least one copy of the parvoviral ITR sequence. In another embodiment, the invention relates to a method for quantifying a nucleic acid impurity in a composition comprising a parvoviral vector, wherein the method consists of the step of determining the relative abundance of a nucleic acid impurity, which nucleic acid impurity comprises a nucleotide sequence that is located between 1-8000 bp, 1-5000 bp, 1-3000 bp, 1-1000 bp, 1-500 bp, 1-250 bp or 1-100 bp immediately adjacent of an parvoviral ITR sequence when the ITR sequence is present in a biological component used in a process for producing the composition and wherein the biological component comprises a transgene flanked by at least one copy of the parvoviral ITR sequence.

As indicated above, during the production process of parvoviral virions a parvoviral sequence can be present in a host cell, a plasmid, a vector and/or a helper virus, wherein preferable the vector is a baculoviral vector. The parvoviral sequence may comprise at least one copy of the ITR and an expression cassette for the expression of a transgene. Overrepresented DNA impurities may comprise any sequence that immediately flank the parvoviral ITR or ITRs, such as genomic sequences, plasmid sequences, vector sequences or sequences of a helper virus. The type of DNA impurity is thus dependent on the sequences flanking the ITR during the production of parvoviral virions. For example, if the parvoviral sequence—comprising at least one copy of the ITR and preferably a transgene—is present in a baculoviral vector, baculoviral sequences immediately flanking the ITR or ITRs will be overrepresented in the composition comprising a parvoviral vector.

In an embodiment of the invention, the nucleic acid impurity is quantified in a composition comprising a parvoviral vector. The method for quantifying the nucleic acid impurity may comprise any method known in the art for quantifying a nucleic acid. Such methods include, but are not limited to, high-throughput sequencing, Q-PCR, limited-cycle PCR, a hybridization assay, a micro-array and an agarose electrophoresis.

In a further embodiment, the biological component is defined as indicated above. In particular, the biological component is selected from a group consisting of a host cell, a plasmid, a vector other than the recombinant parvoviral vector and a helper virus. Preferably, the biological component comprises a parvoviral sequence, wherein preferably the parvoviral sequence comprises at least one ITR and a nucleotide sequence encoding for a transgene. Most preferably, the biological component comprises a nucleotide sequence encoding for a transgene that is flanked by at least one parvoviral ITR on each side.

In the most preferred embodiment the biological component is a vector and wherein the vector is a baculoviral vector. The baculoviral vector preferably comprises a parvoviral sequence. This parvoviral sequence preferably comprises at least one ITR and a nucleotide sequence encoding for a transgene. Most preferably, the baculoviral vector comprises a nucleotide sequence encoding for a transgene that is flanked by at least one parvoviral ITR on each side.

In a method according to the invention, the nucleic acid impurity comprises a nucleotide sequence that is located between 1-10000 bp, 1-9000 bp 1-8000 bp, 1-7000 bp, 1-6000 bp, 1-5000 bp, 1-4000 bp, 1-3000 bp, 1-2000 bp, 1-1000 bp, 1-800 bp, 1-600 bp, 1-500 bp, 1-400 bp, 1-250 bp or 1-100 bp immediately adjacent of an parvoviral ITR sequence when present in a biological component used in a process for producing the composition. The length of the DNA impurity may be dependent on the presence of other randomly packaged DNA impurities and/or on the size of the transgene as there is a maximal packaging capacity of a parvoviral virion. However, it is known that a parvoviral virion may incorporate longer DNA sequences that the length of their own genome (Grieger et al, J Virol. 2005 79(15):9933-44).

In a preferred embodiment of the invention, the parvoviral vector is a recombinant adeno-associated virus (rAAV) vector as described above. Furthermore, the rAAV virion may be produced using any of the production methods as described previously.

In another embodiment, the nucleotide sequence of the nucleic acid impurity is located immediately adjacent on each side of the parvoviral ITR sequence when the ITR sequence is present in a biological component used in a process for producing the composition. The parvoviral sequence present in a biological component may comprise a transgene that is flanked by at least one ITR on each side of the transgene. In such a case, the nucleic acid impurity may comprise nucleotide sequences that are present on one side of the ITRs, i.e. only immediately adjacent the left ITR(s) or only immediately adjacent the right ITR(s). Alternatively, the nucleotide sequence of the nucleic acid impurity may comprise nucleotide sequences that are present on both sides of the ITRs.

In an embodiment of the invention, the nucleic acid impurity comprises a nucleotide sequence that is located immediately adjacent of a parvoviral ITR sequence, when the ITR sequence is present in a biological component used in a process for producing the composition. "Immediately adjacent" is herein defined as follows: In case of an ITR upstream of the transgene, "immediately adjacent" means any nucleotide sequence that ends at least 0, 1, 2, 3, 4, 5, 10, 15, 20, 25, 30, 40, or 50 bp upstream of the ITR. In case the ITR is located downstream of the transgene, immediately adjacent" means any nucleotide sequence that starts at least 0, 1, 2, 3, 4, 5, 10, 15, 20, 25, 30, 40, or 50 bp downstream of the ITR.

Relative Abundance

In an embodiment of the invention, the method comprises the step of determining the relative abundance of a nucleic acid impurity. Relative abundance is herein defined as the presence of (part of) the first nucleic acid molecule in comparison to the presence of (part of) a second nucleic acid molecule in the same or in another composition. In case the relative abundance is determined between two or more compositions, the second nucleic acid molecule may comprise the same or another nucleotide sequence as the first nucleic acid molecule. In case the relative abundance is determined in one composition, the first en second nucleic acid molecules comprise at least partly a different nucleotide sequence.

In the method of the invention, the relative abundance between a nucleic acid impurity and a second nucleic acid molecule is preferably determined in the same composition, although it is also an embodiment of the invention that the relative abundance of a nucleic acid impurity is determined between different compositions. In a preferred method of the invention, the relative abundance is determined as compared to a nucleotide sequence of the parvoviral vector and/or a reference sequence in the composition. Preferably, the transgene and/or reference sequence is present in the same composition as the nucleic acid impurity.

A nucleotide sequence of the parvoviral vector may comprise any sequence of the parvoviral vector, such as the complete parvoviral vector, or (a part of the) nucleotide sequence of the transgene, the promoter or the ITR(s). However, any other nucleotide sequence of the parvoviral vector may be equally suitable for use in the method of the invention.

The reference sequence can be any (part of a) suitable nucleotide sequence. Preferably, the reference sequence is (part of a) sequence of a housekeeping gene, a nucleotide sequence of a biological component and/or the reference sequence is a sequence of a nucleic acid that is used to spike the composition.

In case the reference sequence is a sequence of a biological component, the sequence is not immediately flanking a parvoviral ITR and the reference sequence is preferably derived from a host cell, a plasmid, or a vector used in the process for producing the composition. Preferably, the reference sequence is derived from the same biological component comprising a transgene and at least one ITR. More preferably, the reference sequence comprises a sequence from a baculoviral vector, which baculoviral vector is used in a process for producing the composition, which comprises a transgene and at least one ITR and which reference baculoviral sequence does not immediately flank a parvoviral ITR.

In case the reference sequence is a nucleic acid used to spike the composition, it is intended that this nucleic acid is not present after the production of the composition but is added at later time point, but before determining the relative abundance of the nucleic acid impurity. The nucleic acid molecule used to spike to composition may be any suitable nucleic acid molecule, such as a small linear or circular RNA or DNA molecule of at least 10, 30, 50, 100, 150, 200, 500, 1000 or more base pairs. Such nucleic acid molecule may comprise a coding and/or a non-coding region.

In a further embodiment of the invention, the relative abundance is determined by:
  a) the average number of reads per nucleic acid of the nucleic acid impurity as defined above; and
    i) the average number of reads per nucleic acid of the reference sequence; and/or
    ii) the average number of reads per parvoviral vector in the composition;
  wherein the number of reads is determined by any method as outlined above; and/or
  b) amplification of the nucleic acid impurity as defined above; and
    i) the reference sequence; and/or
    ii) the nucleotide sequence of the parvoviral vector.

In a preferred embodiment the average number of reads is defined as indicated above. In addition, the parvoviral vector may relate to any sequence of the parvoviral vector, such as the complete parvoviral vector, or only (a part of the) nucleotide sequence of the transgene, the promoter or the ITR(s). Furthermore, any other nucleotide sequence of the parvoviral vector may be equally suitable for use in the method of the invention.

In a further embodiment, the relative abundance of the nucleic acid impurity can be determined by any method suitable for determining the quantity of a nucleic acid molecule as indicated above. More preferably, the relative abundance is determined by Q-PCR and/or by high-throughput sequencing. Any Q-PCR method or high-throughput sequencing method that results in the quantification of a nucleic acid is suitable for use in the method of the invention. Q-PCR methods (real-time polymerase chain reactions) are well-known in the art and the technique can either use non-specific fluorochromes or hybridization probes. In a preferred embodiment of the invention, the Q-PCR is performed with specific hybridization probes.

Preferably, the method further comprises the step of a selective hybridization of an oligonucleotide primer to the nucleic acid impurity as defined above.

The selective hybridisation of an oligonucleotide primer to a nucleic acid impurity is understood to mean that the oligonucleotide forms a productive or positive duplex with the nucleic acid impurity. The formation of such a productive or positive duplex is understood as the formation of a duplex between the oligonucleotide and the nucleic acid impurity that can be detected by the formation of an amplicon in the Q-PCR assay. In practice this will mean that the end of the oligonucleotide primer will form a duplex with the nucleic acid impurity, such that the oligonucleotide can be elongated by a polymerase or ligated to an adjacently base paired poly- or oligonucleotide molecule. As used herein, an 'amplicon' relates to a double stranded nucleic acid segment having a defined size and sequence that results from an amplification procedure, such as a PCR procedure. The size of the amplicon is governed by the sites on the two strands of a nucleic acid duplex to which the oligonucleotide primers bind. As explained in U.S. Pat. No. 4,683,195, that segment of the product nucleic acid becomes the prevalent product of the amplification procedure after a small number of cycles of amplification. In addition, a sequence is 'specific' or 'selective' for nucleic acid impurity as long as it hybridises effectively to the target sequence but does not hybridise to any sequence that is not a nucleic acid impurity as defined above, under the conditions used in given experimental circumstances.

In a preferred embodiment, the oligonucleotide primer selectively hybridizes to a nucleic acid impurity comprising a part of a baculovirus sequence or a complement thereof. The term 'complement' or 'complementary sequence' of a first sequence is herein understood to mean the second sequence that can form a double-stranded structure or duplex with the first sequence by matching base pairs, e.g. the complementary sequence to G-T-A-C is C-A-T-G.

It is thus preferred that the nucleic acid impurity is derived from a baculoviral vector used in the process for producing the composition. In particular, it is preferred that such baculoviral vector comprises a transgene flanked by at least one parvoviral ITR. In a preferred embodiment, the oligonucleotide primer selectively hybridizes to a nucleic acid impurity, wherein the nucleic acid impurity comprises a baculovirus-derived nucleotide sequence that is located between 1-10000 bp, 1-9000 bp 1-8000 bp, 1-7000 bp, 1-6000 bp, 1-5000 bp, 1-4000 bp, 1-3000 bp, 1-2000 bp, 1-1000 bp, 1-800 bp, 1-600 bp, 1-500 bp, 1-400 bp, 1-250 bp or 1-100 bp immediately adjacent of the parvoviral ITR sequence, when the parvoviral ITR sequence is present in the baculoviral vector.

Clinical Application

A composition comprising a parvoviral vector should not contain a high degree of nucleic acid impurities, especially if the composition is to be used in a medical treatment. In particular, such nucleic acid impurities could cause adverse reactions in usually already vulnerable patients, which might lead to severe complications. The current invention relates to the discovery that DNA impurities are not randomly encapsulated within a parvoviral virion. Instead, sequences that flank the ITR during the production of parvoviral virions are overrepresented. In another aspect, the current invention therefore relates to a method of determining whether a composition comprising a parvoviral vector is regarded clinically pure, wherein the method comprises the steps of:

i) quantifying a nucleic acid impurity in a composition comprising a parvoviral vector according to any method as outlined above; and ii) determining the composition as being clinically pure if the nucleic acid impurity as defined above is at least 10, 100, 250, 1000 times less present as the reference sequence and/or transgene as determined by the relative abundance of the nucleic acid impurity.

Clinically pure is herein defined as a pharmaceutical high quality product, which is a composition that is regarded as safe for administration to animals, preferably a pharmaceutical high quality product is a product that is regarded as safe for administration to mammals, most preferably the composition is regarded as safe for administration to humans.

In a preferred embodiment of the invention, the nucleic acid impurity as defined above is at least 10, 100, 150, 200, 250, 300, 400, 500, 600, 700, 800, 900, 1000, 10,000 or 100,000 times less present than the transgene or the reference sequence. The presence of the nucleic acid impurity and the transgene or reference sequence can be quantified by any conventional method for quantifying a specific DNA sequence.

Clinically pure is herein further understood that the composition comprising the parvoviral vector is considered pure enough for clinical treatment. In particular, a clinically pure composition according to the invention comprises a low degree of DNA impurities as requested by the International Conference on Harmonisation of Technical Requirements for Registration of Pharmaceuticals for Human Use (ICH) quality and safety guidelines. Preferably, the level of DNA impurity is below a level to cause any adverse effects in patients.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

REFERENCES

1. Fujita, R., Matsuyama, T., Yamagishi, J., Sahara, K., Asano, S., and Bando, H. (2006) Expression of Autographa californica multiple nucleopolyhedrovirus genes in mammalian cells and upregulation of the host beta-actin gene, J. Virol. 80, 2390-2395.
2. Liu, C. Y., Wang, C. H., Wang, J. C., and Chao, Y. C. (2007) Stimulation of baculovirus transcriptome expression in mammalian cells by baculoviral transcriptional activators, J. Gen. Virol. 88, 2176-2184.
3. Laakkonen, J. P., Kaikkonen, M. U., Ronkainen, P. H., Ihalainen, T. O., Niskanen, E. A., Hakkinen, M., Salminen, M., Kulomaa, M. S., Yla-Herttuala, S., Airenne, K. J., and Vihinen-Ranta, M. (2008) Baculovirus-mediated immediate-early gene expression and nuclear reorganization in human cells, Cell Microbiol. 10, 667-681.
4. Blouin, V., Brument, N., Toublanc, E., Raimbaud, I., Moullier, P., and Salvetti, A. (2004) Improving rAAV production and purification: towards the definition of a sealable process, J. Gene Med. 6 Suppl 1, S223-S228
5. Nony, P., Chadeuf, G., Tessier, J., Moullier, P., and Salvetti, A. (2003) Evidence for packaging of rep-cap sequences into adeno-associated virus (AAV) type 2 capsids in the absence of inverted terminal repeats: a model for generation of rep-positive AAV particles, J. Virol. 77, 776-781.
6. Chadeuf, G., Ciron, C., Moullier, P., and Salvetti, A. (2005) Evidence for encapsidation of prokaryotic sequences during recombinant adeno-associated virus production and their in vivo persistence after vector delivery, Mol. Ther. 12, 744-753.
7. Wright, J. F. (2008) Manufacturing and characterizing AAV-based vectors for use in clinical studies, Gene Ther. 15, 840-848.
8. Arsalan Haseeb Zaidi, Patrick J. Bakkes, Jacek Lubelski, Herfita Agustiandari, Oscar P. Kuipers, and Arnold J. M. Driessen (2008) The ABC-Type Multidrug Resistance Transporter LmrCD Is Responsible for an Extrusion-Based Mechanism of Bile Acid Resistance in *Lactococcus lactis* Journal of Bacteriology, 7357-7366
9. Jean-Marie Rouillard, Michael Zuker and Erdogan Gulari (2003) OligoArray 2.0: Design of oligonucleotide probes for DNA microarrays using a thermodynamic approach, Nucleic Acids Research, Vol. 31, No. 12 3057-3062
10. Van Hijum S A., de la Nava G J, Trelles O., Kok J., Kuipers O P., (2003) MicroPreP: a cDNA microarray data pre-processing framework. Appl Bioinformatics, 2(4): 241-4
11. P. Baldi and A. D. Long, (2001) A Bayesian Framework for the Analysis of Microarray Expression Data: Regularized t-Test and Statistical Inferences of Gene Changes, Bioinformatics, 17, 6, 509-519.
12. Krappa, R., Roncarati, R., Knebel-Morsdorf, D., (1995) Expression of PE38 and IE2, Viral members of the C3HC4 finger family, during baculovirus infection: PE38 and IE2 localize to distint nuclear regions, J Virol, 5287-5293.
13. Gerhard Schwarz, Stefan BaEumler, Annette Block, Friedrich G. Felsenstein and Gerhard Wenzel (2004) Determination of detection and quantification limits for SNP allele frequency estimation in DNA pools using real time PCR Nucleic Acids Research, Vol. 32, No. 3 e24
14. Yaffe David, Saxel Ora, (1977) Serial passaging and differentiation of myogenic cells isolated from dystrophic mouse muscle, Nature 270, 725-727
15. Manno, C S, Pierce, G F, Arruda, V R, Glader, B, Ragni, M, Rasko, J et al. (2006). Successful transduction of liver in hemophilia by AAV-factor IX and limitations imposed by the host immune response. Nat Med 12: 342-347.
16. Mingozzi, F, Maus, M V, Hui, D J, Sabatino, D E, Murphy, S L, Rasko, J E et al. (2007). CD8+ T-cell responses to adeno-associated virus capsid in humans. Nat Med 13: 419-422.
17. Christine L. Halbert*, Michael J. Metzger*, Siu-Ling Lam, and A. Dusty Miller (2011) Capsid-expressing DNA in AAV vectors and its elimination by use of an oversize capsid gene for vector production. Gene Ther. 18(4): 411-417
18. Bernd Hauck, Samuel L Murphy, Peter H Smith, Guang Qu, Xingge Liu, Olga Zelenaia, Federico Mingozzi, Jürg M Sommer, Katherine A High and J Fraser Wright (2009)

Undetectable Transcription of cap in a Clinical AAV Vector: Implications for Preformed Capsid in Immune Responses. Mol Ther. 17(1) 144-152

BRIEF DESCRIPTION OF THE FIGURES

FIG. 1 FIGS. 1A-1F. Resistance of AAV1-transgene (upper panels) and baculovirus DNA (middle and lower panels) to DNAse I. The amount of DNA as detected by Q-PCR using three different primer sets either without or with DNAse treatment. For each primer set two batches were tested. A) and B) primer set 59/60, C) and D) primer set 180/181, E) and F) primer set 340/341.

FIGS. 4A-4C. rAAV comprising a transgene was analyzed by deep-sequencing. The obtained reads were aligned to the transgene (A), the cap cassette (B), or the rep cassette (c).

FIG. 6. Five different batches of rAAV vectors were tested for DNA impurities using Q-PCR or deep-sequencing with Illumina or Roche 454.

EXAMPLES

Example 1

Figure 1A:
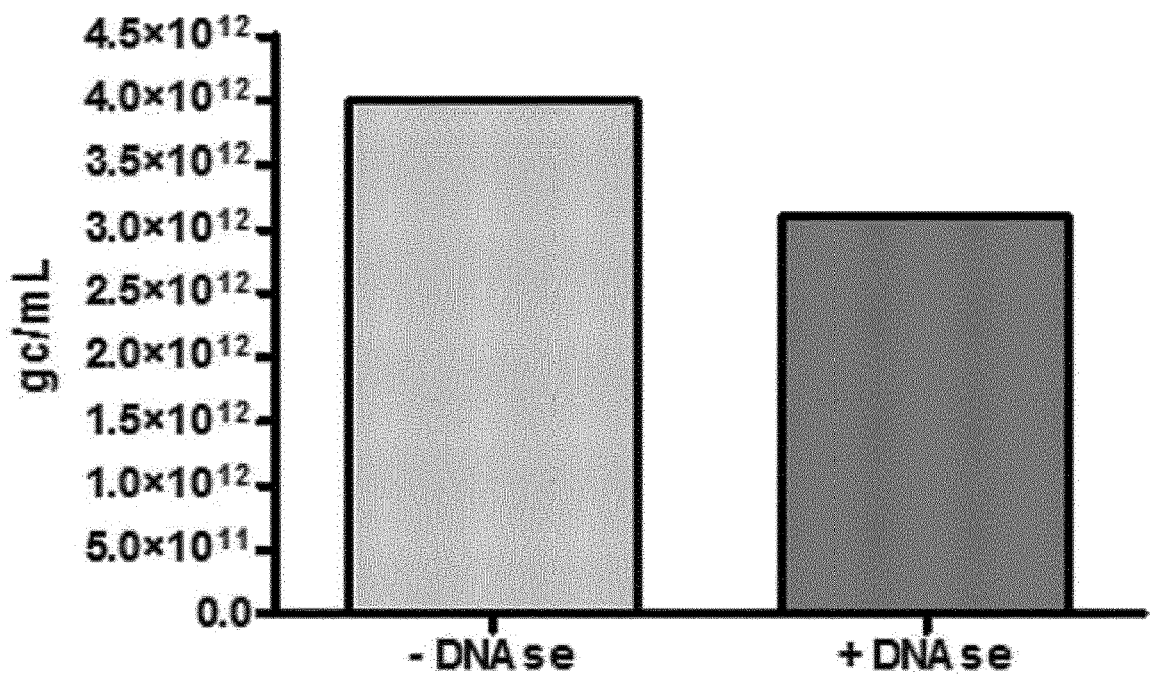
Figure 1B:
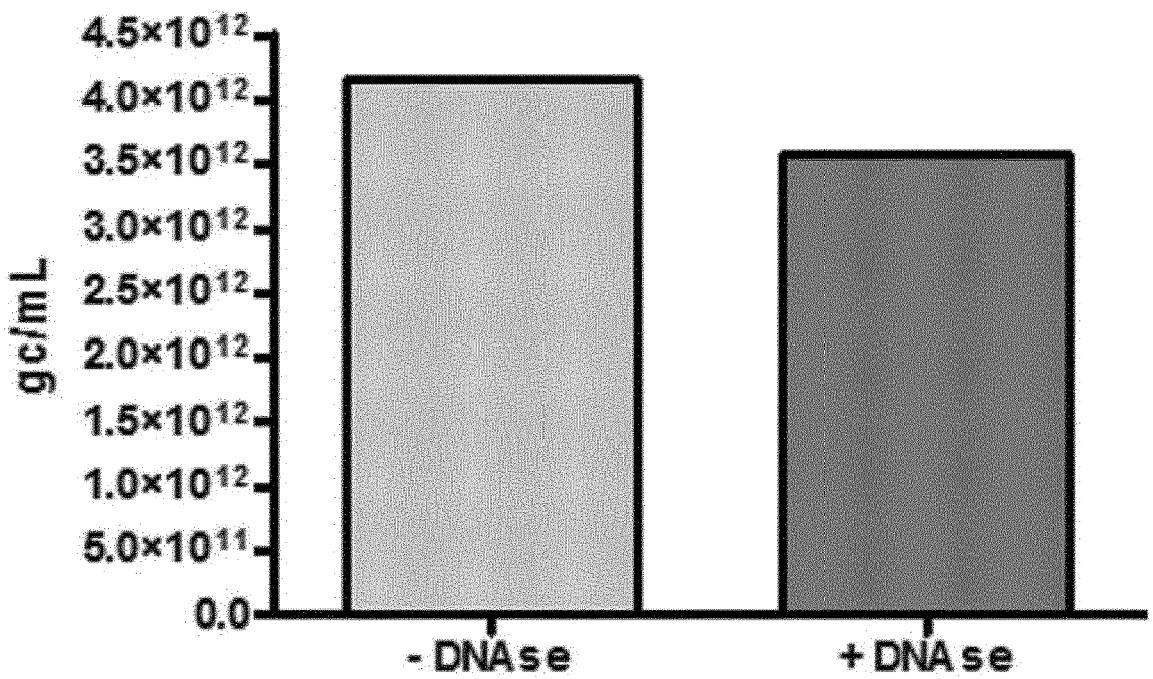
Figure 1C:
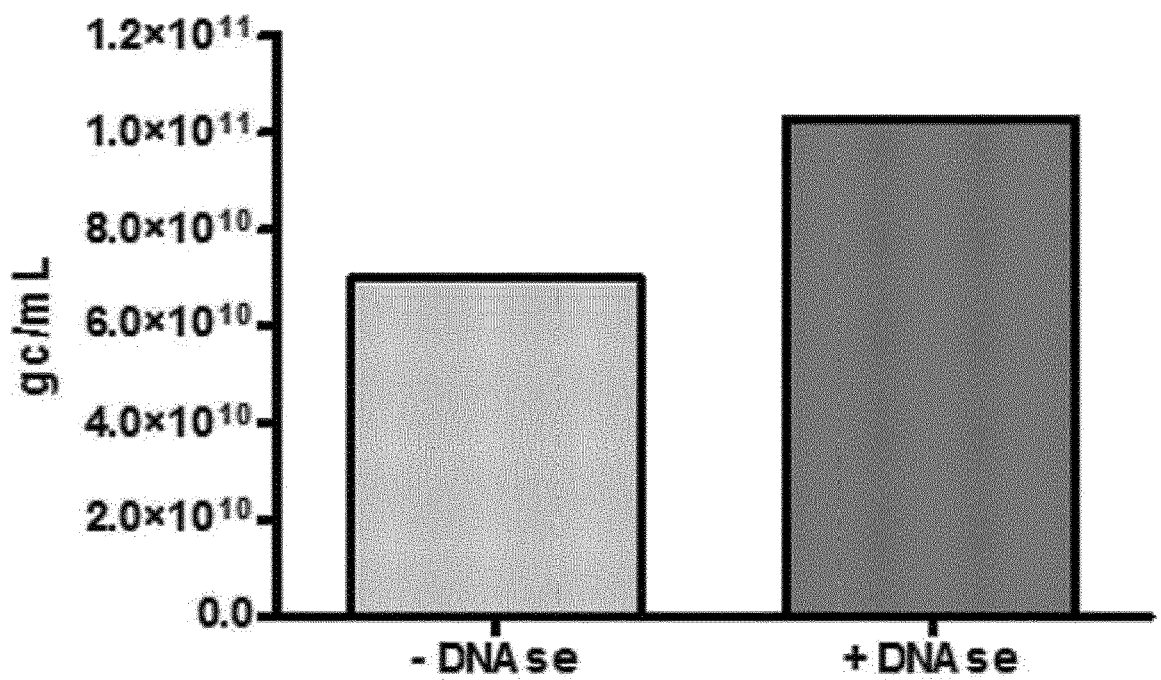
Figure 1D:
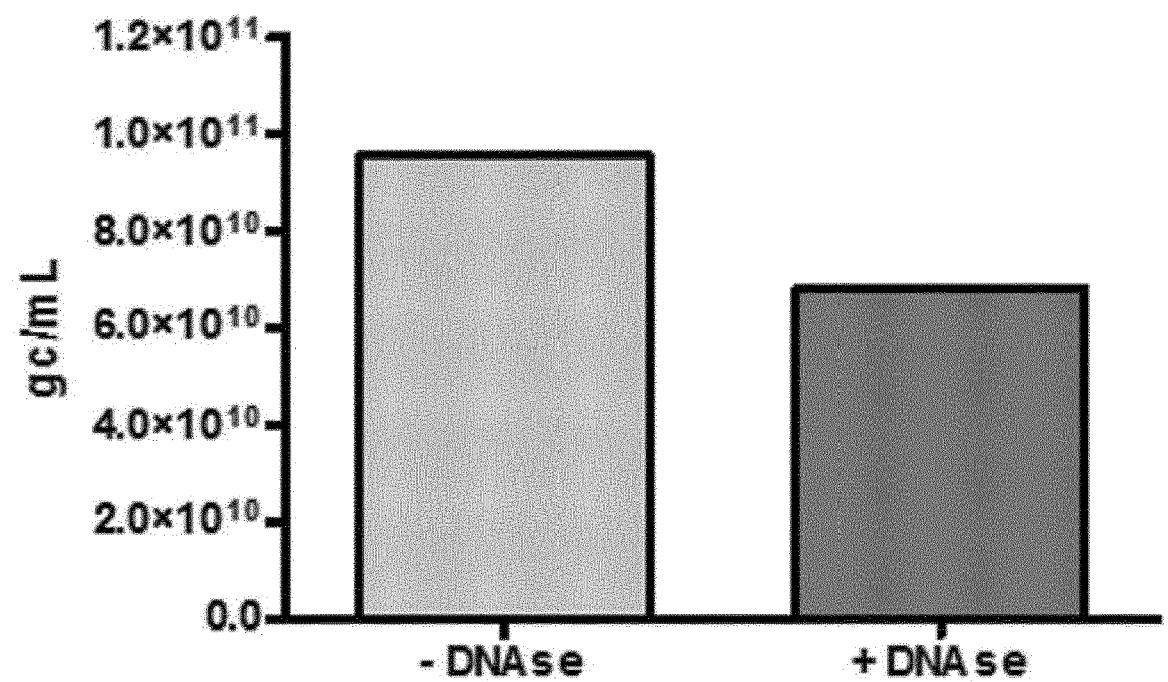
Figure 1E:
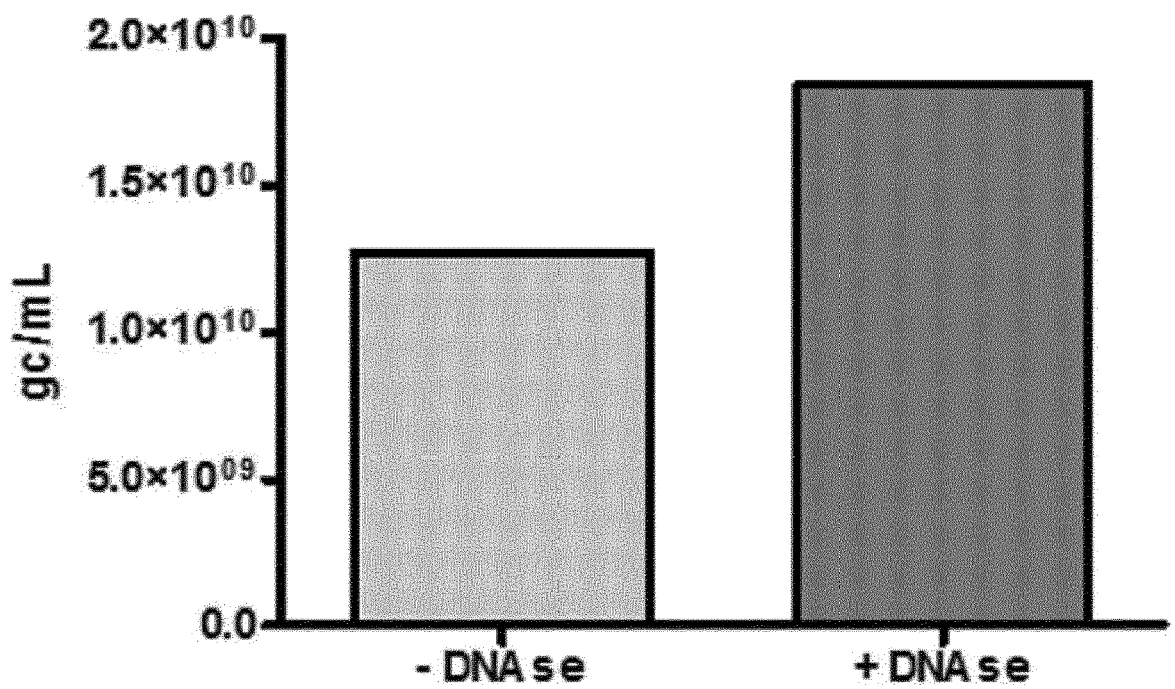
Figure 1F:
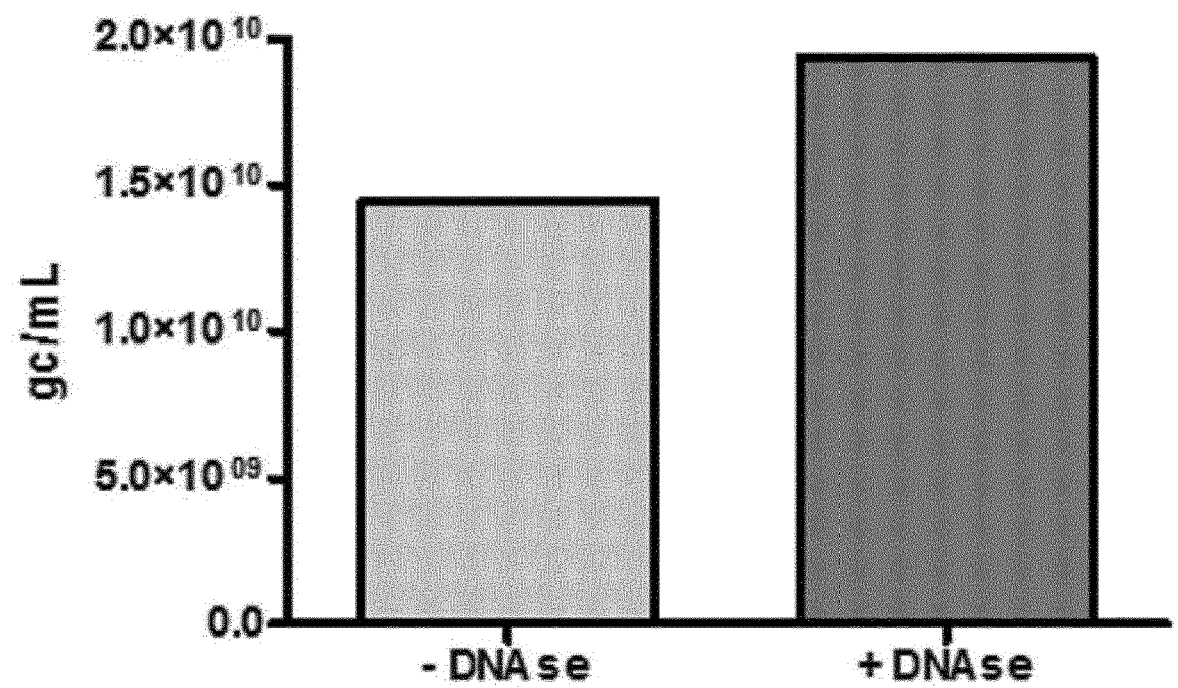

DNA Impurities in Manufactured rAAV Vectors 1.1 Material and Methods

To investigate whether the residual DNA was packaged in AAV1 particles, it was tested whether the residual DNA was DNAse resistant. The samples were treated with Benzonase (9 U/mL) and the amount of DNA was analyzed using Q-PCR.

DNA was isolated from the samples followed by Q-PCR using three different primer sets (59/60, 180/181, 340/341). To study the DNAse resistance of the baculovirus DNA, for some samples the DNAse step was omitted (indicated as without DNAse). The data were analyzed using PLA analysis and for each sample the ratios of the amounts of DNA amplified by the different primer sets was determined.

The amount of AAV1 DNA was determined using Q-PCR with primer set 59/90 targeting the CMV promoter of the AAV1-transgene vector. The quantification of residual baculovirus DNA was performed using Q-PCR with baculovirus-specific primers. The experiments were performed using two different primer sets; primer set 180/181 targets ORF 1629 of the baculovirus DNA close to AAV-transgene cassette and primer set 340/341 targets the hr3 sequence of baculovirus, detecting baculovirus DNA located distantly from the AAV1-transgene cassette. For these experiments two standards were included: plasmid standard line (pVD) and purified baculovirus DNA of clone VD.

To determine the amount of baculovirus DNA using primer set 180/181, pVD with primer set 180/181 was used as standard. The concentration of pVD was determined with OD measurements. To determine the amount of baculovirus DNA using primer sets 340/341, BacVD with primer set 340/341 was used as standard. The amount of BacVD for the standard line was determined by Q-PCR using primer set 180/181 with pVD as standard.

The amount of DNA (gc/mL) was calculated using the formula:

$$[DNA] = S \cdot D \cdot C$$

in which:
S=mean quantity measured (gc)
D=Dilution factor of viral DNA (either 500 times or 1000 times)
C=Correction factor to calculate from 10 µl sample to 1 mL sample (100)

To calculate the amount of DNA in µg/mL, the formula was extended to:

$$[DNA] = \frac{S \cdot D \cdot C \cdot X}{A} \cdot Mw \Rightarrow \ldots \mu g/mL$$

in which:
X=Conversion factor for g to µg ($10^6$)
A=Number of Avogadro ($6.022 \times 10^{23}$)
Mw=Molar weight of DNA. The baculovirus genome consists of 135 kbp double stranded DNA. Mean molar weight per bp is 649 Da. As Mw for the baculovirus DNA (after determination using primer sets 180/181 or 340/341), a Mw of $135000 \cdot 649 = 8.76 \times 10^7$ Da was used.

The AAV1 genome consists of 3630 bp single stranded DNA. To calculate the amount of AAV1 DNA, a Mw of $3630 \text{ bp} \cdot 340 \text{ Da} = 1.23 \times 10^6$ Da was used.

1.2 Results

The amount of baculovirus DNA was determined with Q-PCR using two different primer sets. Primer set 180/181 detects a sequence in the ORF 1629, close to the AAV-transgene cassette, while the sequence for primer set 340/341 is located distantly from the cassette. The results in Table 1 show that the two primer sets yield very different values for the amount of gc/mL of baculovirus DNA (primer set 180/181 yields on average 20-fold higher values than obtained by primer set 340/341).

TABLE 1

Concentration of intended rAAV genome and contaminating DAN

| Batch | AAV DNA (primers 59 . . . 90) | baculovirus DNA (primer 180 . . . 181) | baculovirus DNA (primer 340 . . . 341) |
|---|---|---|---|
| 1 | $5.9 \times 10^{12}$ | $3.2 \times 10^{11}$ | $1.4 \times 10^{10}$ |
| 2 | $5.6 \times 10^{12}$ | $2.9 \times 10^{11}$ | $1.5 \times 10^{10}$ |
| 3 | $6.5 \times 10^{12}$ | $3.0 \times 10^{11}$ | $1.3 \times 10^{10}$ |
| 4 | $7.1 \times 10^{11}$ | $3.7 \times 10^{10}$ | $1.5 \times 10^{9}$ |
| 5 | $7.0 \times 10^{12}$ | $3.0 \times 10^{11}$ | $1.2 \times 10^{10}$ |
| 6 | $8.5 \times 10^{11}$ | $3.5 \times 10^{10}$ | $2.7 \times 10^{9}$ |
| 7 | $9.1 \times 10^{12}$ | $3.0 \times 10^{11}$ | $2.0 \times 10^{10}$ |
| 8 | $8.9 \times 10^{11}$ | $3.9 \times 10^{10}$ | $2.0 \times 10^{9}$ |
| 9 | $8.4 \times 10^{11}$ | $3.9 \times 10^{10}$ | $1.9 \times 10^{9}$ |
| 10 | $1.1 \times 10^{12}$ | $3.6 \times 10^{10}$ | $1.7 \times 10^{9}$ |
| 11 | $3.0 \times 10^{12}$ | $1.3 \times 10^{11}$ | $5.8 \times 10^{9}$ |

TABLE 1-continued

Concentration of intended rAAV genome and contaminating DAN

| Batch | AAV DNA (primers 59 . . . 90) | baculovirus DNA (primer 180 . . . 181) | baculovirus DNA (primer 340 . . . 341) |
|---|---|---|---|
| 12 | $3.3 \times 10^{12}$ | $1.3 \times 10^{11}$ | $5.9 \times 10^9$ |
| 13 | $2.9 \times 10^{12}$ | $1.2 \times 10^{11}$ | $6.1 \times 10^9$ |

The concentration of the Bac.VD standard was corrected using Q-PCR, it can thus be excluded that this difference is standard related. Therefore, these data indicate that the baculovirus DNA close to the ITRs (detected with primer set 180/181) is far more present than DNA distant from the ITRs (detected by the primer set 340/341).

Example 2

Determining Nucleic Acid Impurities Using Q-PCR 2.1 Material and Methods

Figure 2:
FIG. 2. Sequence map of the baculoviral plasmid Bac.VD. The used primer sets and ITRs are indicated.

To further investigate which parts of the baculovirus genome were present in the samples and possible differences in the amount of different sequences, Q-PCR with different primer sets (See FIG. 2) was performed. For each primer set a standard line was included in the experiment. The amount of transgene copies was determined using primer set 59/60. Subsequently, the relative amount of genome copies as compared to transgene copies was determined. Since it is known that AAV particle may incorporate longer DNA sequences than the length of its own genome (Grieger et al. 2005, Allocca et al. 2008) the primers were chosen at the start and the end of the ORFs flanking the transgene cassette and 10 kb up- and downstream of the ITRs.

2.2 Results

Figure 3:
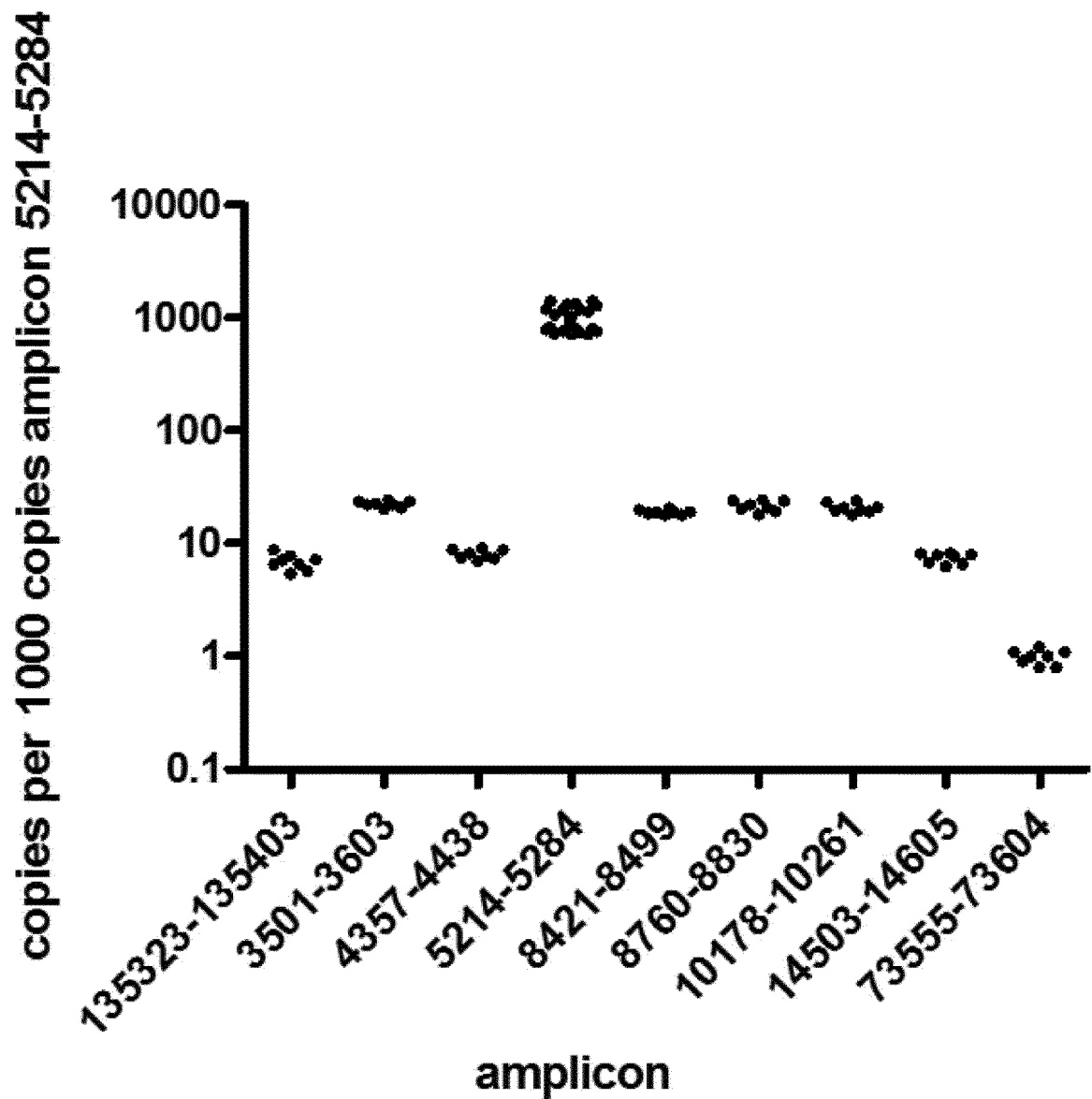
FIG. 3. Relative amount of genome copies as detected by the different primers sets. On the axis the location of the amplicons are indicated. Amplicon 5214-5284 represents the CMV promoter of the AAV-transgene cassette. Amplicon 73555-73604 is targeted by primer set 340/341 and located the furthest from the AAV-transgene cassette. Each dot represents one measurement.

The amount of baculovirus DNA was determined using primer set 340/341, amplifying amplicon 73555-73604 that is located close to the hr3 sequence of the baculovirus. It was assumed that the amount of genome copies determined with these primers is representative of the entire baculovirus genome. However, similar experiments using different primer sets targeting sequences closer to the AAV-transgene cassette showed that a higher number of genome copies was found when the amplicon was located closer to the AAV-transgene cassette containing the ITRs (FIG. 3). Since it is known that AAV may be able to package larger DNA sequences (up to 8.9 kb, probably even higher (Allocca et al., 2008)), we expect that these sequences are packaged inside the particle. This implies that there are two kinds of residual baculovirus DNA sequences; 1) random sequences, as we determined with primer set 340/341, which are only found in 0.1% of the amount of genome copies of the transgene and 2) baculovirus sequences within 10 kb from the transgene cassette (within the range of AAV packaging limit), which are found in-between 1 and 2.5% of the amount of transgene genome copies. Both sequences are presumably packaged inside the AAV1 particle or associated with the capsid.

Example 3

Determining Nucleic Acid Impurities Using Next Generation Sequencing 3.1 Material and Methods To investigate the extent and origin of the DNA impurities in manufactured rAAV vectors, four different batches of rAAV vectors were analyzed by deep-sequencing. DNA was isolated from these rAAV vectors using the NUCLEOSPIN® extract II kit (Macherey Nagel, Duren, Germany).

This DNA was used to prepare the deep-sequencing libraries.

In order to create separate sequencing features an in situ hybridization is performed. Clusters are accomplished by limiting dilutions of an initial material. The DNA fragments are melted and the single strands are trapped inside the flow cell which is covered by a dens lawn of primers. Subsequent local amplification (bridge PCR) leads to formation of cluster of approximately 1000 identical molecules per square micrometer. The base incorporation starts by adding primers, polymerase and four flourophore-labeled deoxynuclotidetriphosphates. The dNTPs act as reversible terminators, i.e. only a single base is added per molecule in each cycle. The cluster fluorescence is measured to identify which base has been incorporated. A green laser identifies the incorporation of the bases G and T and a read laser identifies the bases A and C. Two different filters are used to distinguish between G/T and A/C, respectively. After the signal detection the fluorophor and the terminating modification of the nucleotide are removed (Dohm, J. C., Lottaz, C., Borodina, T., and Himmelbauer, H. (2008), *Nucleic Acids Res.* 36, e105; Shendure, J. and Ji, H. (2008), *Nat. Biotechnol.* 26, 1135-1145; Rothberg, J. M. and Leamon, J. H. (2008), *Nat. Biotechnol.* 26, 1117-1124; Kahvejian, A., Quackenbush, J., and Thompson, J. F. (2008), *Nat. Biotechnol.* 26, 1125-1133). This method can be particularly useful to determine what type of sequence is present as an impurity and what the ratios between the specific sequence populations are. The analysis was performed by ServiceXS (Leiden).

Figure 4A:
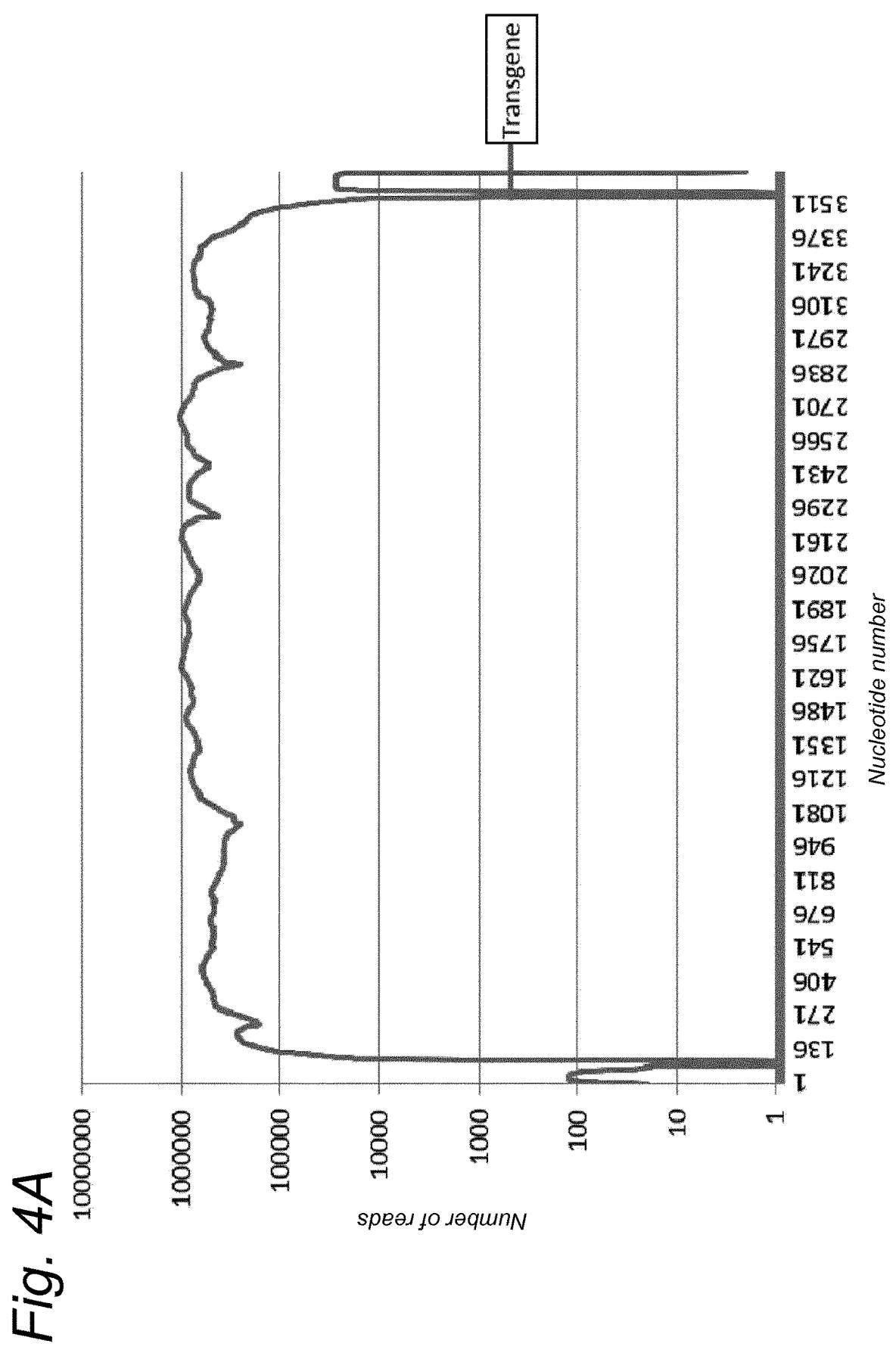
Figure 4B:
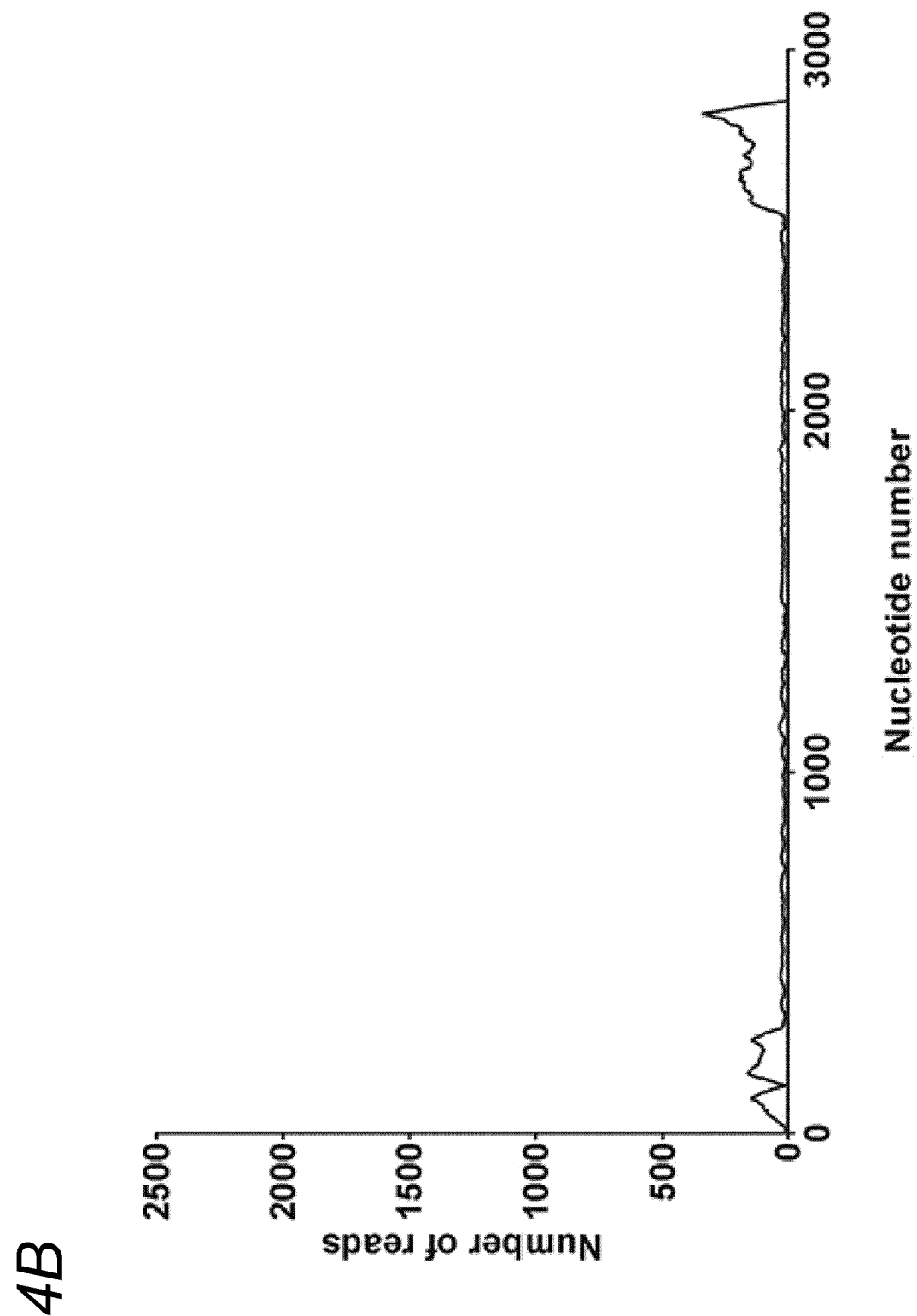
Figure 4C:
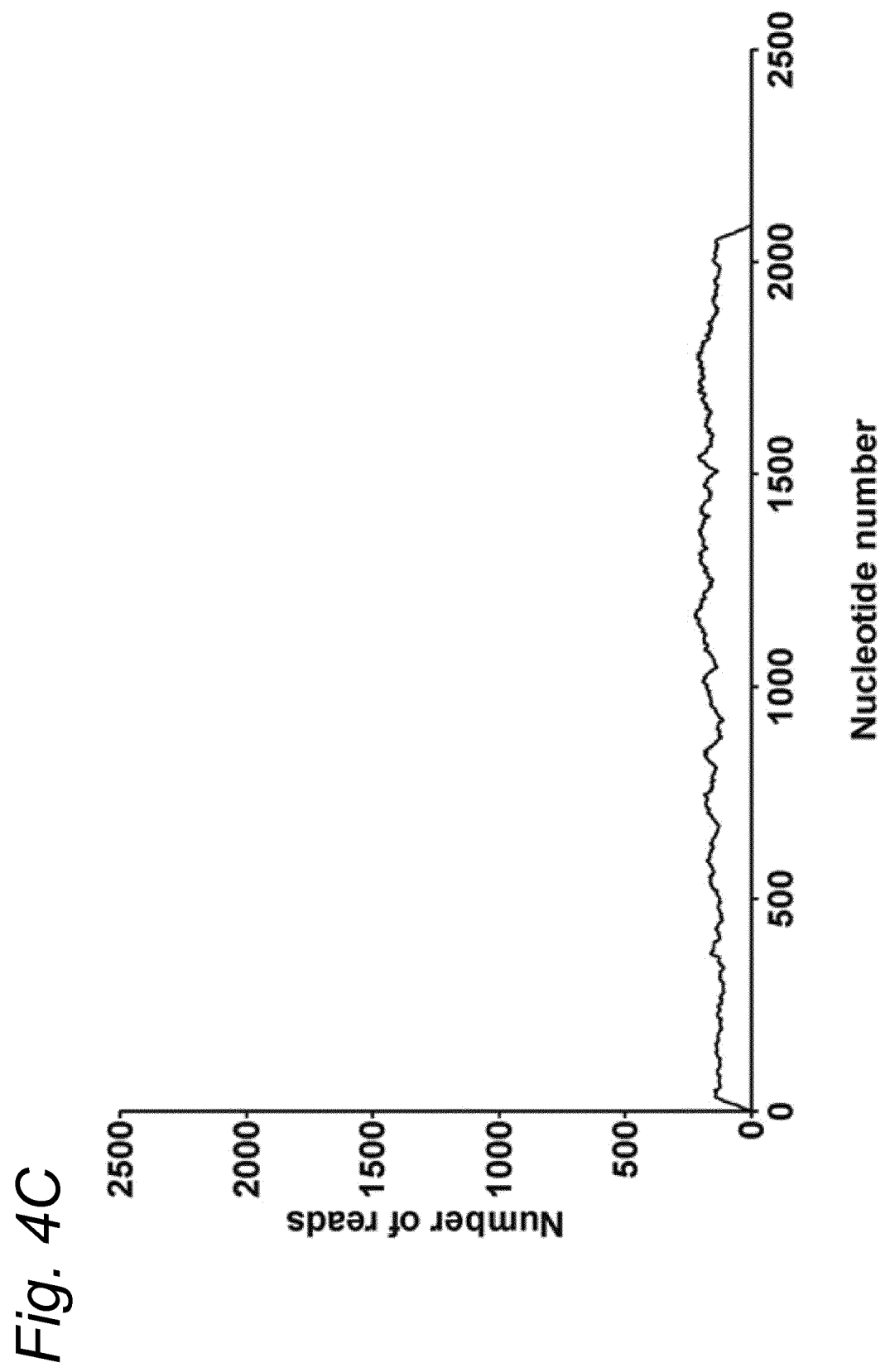

Standard next generation sequencing experiment results in >20 million of short reads which needs to be aligned to a reference sequence or de novo assembled in order to produce contigs. Here, upon sequencing of the total content, reads were aligned to a number of reference sequences. These reference sequences represent DNA molecules which are known to be present in the rAAV vector preparations. This includes the intended genome and production related DNA impurities. The alignment was performed by CLC_bio aligner. The frequency at which every base is read in the experiment provides information about its relative occurrence as compared to other measured sequences. The reads per nucleotide were retrieved for each reference sequence (FIGS. 4A-4C). It is generally accepted that when nucleotides of the reference sequence are read more then 8-12 times, the sequence information has a high confidence level (Schuster, S. C. (2008), *Nat. Methods* 5, 16-18).

3.2 Results

Total DNA sequencing was used to analyse the DNA composition of different AAV batches. The analysis was performed by Baseclear (Leiden, The Netherlands) based on a single read sequencing procedure of Illumina GAI-II. Resulting quality trimmed raw sequence data were analyzed with a help of CLC_bio bioinformatic software. The reads were reference assembled onto the reference sequences representing the potentially presented DNA molecules in rAAV vector preparations i.e. baculovirus backbone, cap specific, rep specific and transgene specific DNA. As expected great majority >99.7% of generated 20 million reads assembled to the intended DNA transgene cassette and to the known production related DNA impurities. All other sequences (below 0.3%) which were not assembled to any of the mentioned reference sequences may represent sequencing errors, linker multimerization, low quality reads and other DNA sequences.

Figure 5:
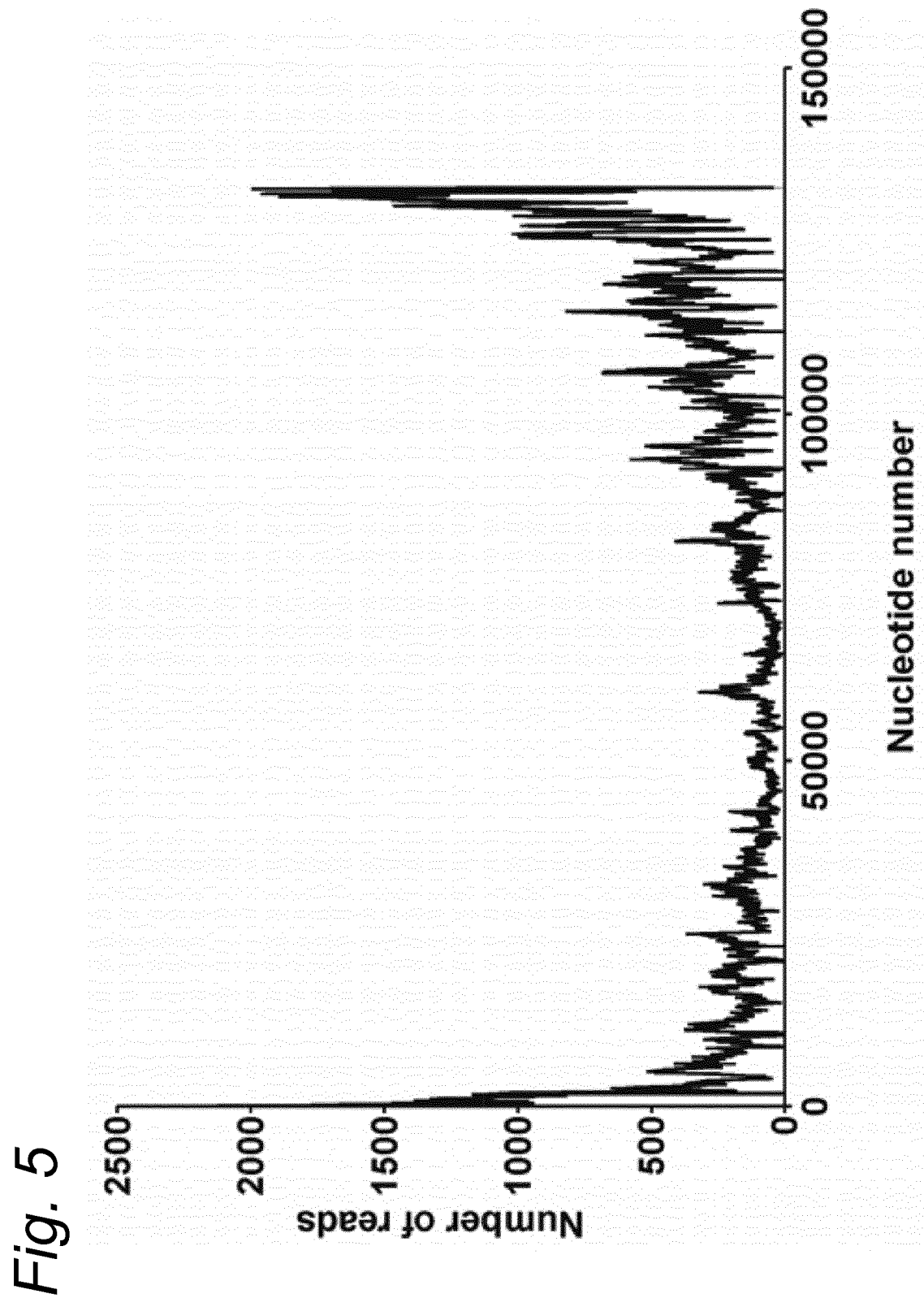
FIG. 5. rAAV was analyzed by deep-sequencing. The obtained reads were aligned to the baculoviral genome. Depicted is the distribution of reads per nucleotide of the baculoviral backbone. Nucleotide 1 is the right ITR as indicated in FIG. 2.

Counts per nucleotide were retrieved for transgene cassette, cap cassette, rep cassette and baculovirus genome and plotted against a nucleotide number (see FIGS. 4 and 5). The distribution of the read frequencies per nucleotide was highly consistent between the different batch preparations. Furthermore, it became evident that the distribution of baculovirus genome is not random. The genome segments flanking ITRs were clearly overrepresented (FIG. 5).

We have used an average distribution of the reads retrieved from sequencing experiments as an input for calculating the relative occurrence of various DNA sequences found in rAAV preparations (table 2).

TABLE 2

Average read distribution (S) in 5 different rAAV batches (lot #)

|  | Lot#1 | Lot#2 | Lot#3 | Lot#4 | Lot#5 |
|---|---|---|---|---|---|
| transgene cassette | 569837 | 588620 | 600677 | 589597 | 544717 |
| Baculovirus | 1184 | 1449 | 1236 | 1316 | 1087 |
| Cap cassette | 60 | 47 | 43 | 102 | 46 |
| Rep cassette | 460 | 676 | 596 | 691 | 562 |

Table 2 shows average frequencies (S) retrieved per given sequence. These frequencies are presented in relation to the main DNA in the sample i.e. transgene cassette in Table 3. Percentage of a given impurity is calculated in relation to the transgene cassette according to the formula presented below and takes in to account size correction factor.

$$X_{bac} = S_{bac}/S_{transgene} * C_{bac} * 100\%$$

Where:

$X_{bac}$—percentage of DNA impurities of baculovirus in relation to transgene cassette $S_{bac}$—average counts retrieved for baculovirus backbone $S_{transgene}$—average counts retrieved for transgene cassette $C_{bac}$—molecule length correction factor where $C_{bac}$=baculovirus backbone length (nt)/transgene cassette length (nt)

TABLE 3

Relative abundance of the various DNA impurities as compared to transgene cassette. Average count distribution (S) of different molecules are presented in relation to the count distribution trasngene ($S_{transgene}$)

|  | $S_{transgene}/S_{transgene}$ | $S_{bac}/S_{transgene}$ | $S_{cap}/S_{transgene}$ | $S_{rep}/S_{transgene}$ |
|---|---|---|---|---|
| Lot#1 | 1 | 2.077E−03 | 1.048E−04 | 8.073E−04 |
| Lot#2 | 1 | 2.462E−03 | 8.068E−05 | 1.148E−03 |
| Lot#3 | 1 | 2.057E−03 | 7.207E−05 | 9.918E−04 |
| Lot#4 | 1 | 2.232E−03 | 1.727E−04 | 1.173E−03 |
| Lot#5 | 1 | 1.996E−03 | 8.467E−05 | 1.031E−03 |

TABLE 4 percentage of various impurities present in various AAV batches in relation to lpl cassette (based on the formula described in the text).

|  | transgene | rep | cap | Baculovirus backbone |
|---|---|---|---|---|
| Molecular length (nt) | 3645 | 2785 | 3088 | 133894 |
| Molecular length correction factor (C) | 1 | 0.76406 | 0.847188 | 36.73361 |
| % of transgene present in batch 1 | N/A | 0.061682% | 0.00888% | 7.630121% |
| % of transgene present in batch 2 | N/A | 0.087726% | 0.006835% | 9.04252% |
| % of transgene present in batch 3 | N/A | 0.075782% | 0.006106% | 7.555691% |
| % of transgene present in batch 4 | N/A | 0.089591% | 0.01463% | 8.200541% |
| % of transgene present in batch 5 | N/A | 0.078764% | 0.007173% | 7.333003% |

Example 4

Non-Random Distribution of the DNA Impurities 4.1 Material and Methods

The next step was to determine the exact origin of the Baculovirus-obtained DNA impurities. To this end, different batches of rAAV vectors were deep-sequenced on the Illumina platform as described above. Alignment of the reads to the baculovirus genome provided a means to examine the frequency of each (baculovirus-derived) nucleotide in the deep-sequencing library. In addition, the average frequency was calculated by dividing the total number of reads that mapped to the baculovirus genome with the number of nucleotides.

4.2 Results

FIG. 5 depicts the alignment of the reads to the Baculovirus genome after deep-sequencing. If the DNA impurities would be derived randomly from Baculovirus genome, a relatively even distribution should be observed with about 1200 reads per nucleotide. An even distribution is indeed seen in the middle of the baculovirus genome. However, at the beginning and at the end of the Baculovirus genome a strong increase in read number is observed. This indicates that these regions are overrepresented as DNA impurities in rAAV.

Example 5

Quality Control Assessment Using Q-PCR or Deep-Sequencing 5.1 Material and Methods In order to investigate the quantitative capabilities of different NGS methodologies, namely SOLEXA® and 454 Roche, the obtained NGS read distribution was compared to the measurements of various targets located across the baculovirus genome with qPCR (FIG. 6). QPCR targets represent regions: highly overrepresented (180/181), matching the average distribution (426/427, 428/429; 1018/1019; 1020/1021; 1024/1025) and underrepresented (340/341). The latter region was used as a calibrator for all the other measurements.

5.2 Results

Three different techniques were investigated to test the level of DNA impurity in rAAV vectors. As shown in FIG. 6, the three techniques correlated well with each other and can thus be used side-by-side for the detection of DNA impurities in rAAV vectors.

As indicated in FIG. 6, NGS analysis clearly demonstrates that the random choice of DNA amplicon for a quantitative PCR can lead to inaccurate measurement of a particular DNA impurity in the vector preparation. The presence of a given DNA impurity is calculated based on the amplicon measurement under the assumption that all the parts of the investigated DNA molecule (which sometimes are 136000 bp long e.g. baculovirus backbone) are distributed with the same frequency. Here presented analysis clearly indicates that various segment of long DNA molecules e.g. baculovirus genome, may contaminate vector preparation with different frequencies due to unequal packaging of different DNA sequences.

TABLE 5

Q-PCR primers used in the experiments

| SEQ ID NO | Name | Sequence | Target | direction | amplicon |
|---|---|---|---|---|---|
| 7 | pr59 | AATGGGCGGTAGGCGTGTA | CMV promoter | forward | 5214-5284 |
| 8 | pr60 | AGGCGATCTGACGGTTCACTAA | CMV promoter | reverse | 5214-5284 |
| 9 | pr180 | CGAACCGATGGCTGGACTATC | Orf 1629 (protein sciences baculo system) | forward | 8760-8830 |
| 10 | pr181 | TGCTGCTACAAGATTTGGCAAGT | Orf 1629 (protein sciences baculo system) | reverse | 8760-8830 |
| 11 | pr340 | ATACAACCGTTGGTTGCACG | hr3 region baculo downstream | forward | 73555-73604 |
| 12 | pr341 | CGGGACACGCCATGTATT | hr3 region baculo downstream | reverse | 73555-73604 |
| 13 | pr402 | GGGAGTGGCGGCGTTGATTT | Baculovirus DNA 10 kb left | sense | 135323-135403 |
| 14 | pr403 | GCACAGTTCAAGCCTCACAGCCTA | Baculovirus DNA 10 kb left | antisense | 135323-135403 |
| 15 | pr404 | CAAACGTGGTTTCGTGTGCCAA | Baculovirus DNA left ORF603 | sense | 3501-3603 |
| 16 | pr405 | GATGCATGACTTCACCCACACACTT | Baculovirus DNA left ORF603 | antisense | 3501-3603 |
| 17 | pr406 | ACAGCCATTGTAATGAGACGCACAA | Baculovirus DNA right ORF603 | sense | 4357-4438 |
| 18 | pr407 | CCTAGCGCCCGATCAGCAACTATAT | Baculovirus DNA right ORF603 | antisense | 4357-4438 |
| 19 | pr408 | TACCGACTCTGCTGAAGAGGAGGAA | Baculovirus DNA left ORF1629 | sense | 8421-8499 |
| 20 | pr409 | TGCGTCTGGTGCAAACTCCTTTA | Baculovirus DNA left ORF1629 | antisense | 8421-8499 |
| 21 | pr410 | GATTCGTCATGGCCACCACAAA | Baculovirus DNA right ORF 1629 | sense | 10178-10261 |
| 22 | pr411 | CCAAAGCGCCCGTTGATTATTTT | Baculovirus DNA right ORF 1629 | antisense | 10178-10261 |
| 23 | pr412 | GCGTACTTGCGGCTGTCGTTGTA | Baculovirus DNA 10 kb right | sense | 14503-14605 |
| 24 | pr413 | CGAGGTCAAGTTCAAAGGGCAACAT | Baculovirus DNA 10 kb right | antisense | 14503-14605 |
| 25 | Pr426 | GCATTTCGCAGCTCTCCTTCAATT | Bac genome | sense | 32837-32935 |
| 26 | Pr427 | CTTCAAGCGAGAACGCAGCAATT | Bac genome | antisense | 32837-32935 |
| 27 | Pr428 | GTGGCGTTTGCCGTGGAAAA | Bac genome | sense | 116615-116699 |
| 28 | Pr429 | TGCAGCTGTGCGTTTTGAATGAA | Bac genome | antisense | 116615-116699 |
| 29 | Pr1018 | TTGTTATGTCAATTTGTAGCGC | Bac genome | sense | 18230-18296 |
| 30 | Pr1019 | TGCATAAAGACACAGTACAACG | Bac genome | antisense | 18230-18296 |
| 31 | Pr1020 | GACATAGTTCGTTTGAAAATTATCCC | Bac genome | sense | 25963-26024 |

TABLE 5-continued

Q-PCR primers used in the experiments

| SEQ ID NO | Name | Sequence | Target | direction | amplicon |
|---|---|---|---|---|---|
| 32 | Pr1021 | AACGATCAAGCTGTTAATAAACG | Bac genome | antisense | 25963-26024 |
| 33 | Pr1024 | CGCTTCGGCGTAGTTTACC | Bac genome | sense | 109100-109151 |
| 34 | Pr1025 | CGCTATAAGCGCGGGTTAC | Bac genome | antisense | 109100-109151 |

The invention claimed is:

1. A method for identifying and quantifying a nucleic acid impurity in a composition comprising a parvoviral vector, comprising:
   (a) subjecting the composition to nucleic acid sequencing to obtain at least a thousand random reads of nucleotide sequences;
   (b) comparing, using a processor, the at least a thousand random reads from step (a) with a nucleotide sequence of a biological component used in a process for producing the composition, whereby a match between a random read and a nucleotide sequence of a biological component identifies a nucleic acid impurity;
   (c) determining an average number of reads per parvoviral vector;
   (d) determining a distribution of reads by calculating a number of reads per nucleotide of an identified nucleic acid impurity;
   wherein an identified nucleic acid impurity is identified as an overrepresented impurity when the distribution of reads is not random and the number of reads per nucleotide of a nucleic acid impurity is at least 0.001% the average number of reads per parvoviral vector.

2. The method according to claim 1, wherein the nucleic acid sequencing in step (a) comprises high-throughput sequencing.

3. The method according to claim 1, wherein the parvoviral vector is a recombinant adeno-associated virus (rAAV) vector.

4. The method according to claim 1, wherein the nucleotide sequence of a biological component is selected from a group consisting of nucleotide sequences of: a host cell, a plasmid, a vector other than the recombinant parvoviral vector, and a helper virus.

5. The method according to claim 4, wherein the nucleotide sequence of a biological component is a baculoviral vector.

6. The method according to claim 4, wherein the helper virus is a recombinant adenovirus and/or a recombinant herpes simplex virus.

7. The method according to claim 1, wherein the nucleotide sequence of the biological component comprises a nucleotide sequence encoding for Rep, Cap and/or a transgene.

8. The method according to claim 7, wherein the transgene is flanked by at least one parvoviral ITR.

9. The method according to claim 1, wherein the overrepresented nucleic acid impurity is quantified in a second or further composition.

10. The method according claim 1, wherein the composition comprising the parvoviral vector comprises a parvoviral capsid wherein the parvoviral vector is packaged.

11. The method according to claim 1, wherein the composition comprising the parvoviral vector does not consist of a sample from a mammal.

* * * * *